(12) United States Patent
Chila et al.

(10) Patent No.: US 11,518,615 B2
(45) Date of Patent: Dec. 6, 2022

(54) INVENTORY SYSTEM AND METHODS OF USING THE SAME

(71) Applicant: Ethicon, Inc., Somerville, NJ (US)

(72) Inventors: Matthew Chila, Doylestown, PA (US); Jonathan Addeo Syby, Manasquan, NJ (US); Allen Keith On, Flemington, NJ (US); David Mickle Wade, Boca Raton, FL (US)

(73) Assignee: Ethicon, Inc., Raritan, NJ (US)

( * ) Notice: Subject to any disclaimer, the term of this patent is extended or adjusted under 35 U.S.C. 154(b) by 288 days.

(21) Appl. No.: 16/887,908

(22) Filed: May 29, 2020

(65) Prior Publication Data

US 2020/0377300 A1 Dec. 3, 2020

Related U.S. Application Data

(60) Provisional application No. 62/854,012, filed on May 29, 2019.

(51) Int. Cl.
| | |
|---|---|
| *B65G 1/137* | (2006.01) |
| *A61B 90/90* | (2016.01) |
| *G16H 40/67* | (2018.01) |
| *G16H 40/20* | (2018.01) |
| *B65G 1/04* | (2006.01) |

(Continued)

(52) U.S. Cl.
CPC ............ *B65G 1/1371* (2013.01); *A61B 90/90* (2016.02); *B65G 1/0485* (2013.01); *G06K 7/10366* (2013.01); *G06K 7/1413* (2013.01); *G06K 7/1417* (2013.01); *G06Q 10/0875* (2013.01); *G06Q 30/014* (2013.01); *G16H 40/20* (2018.01); *G16H 40/67* (2018.01); *H04N 5/76* (2013.01); *A61B 17/06114* (2013.01)

(58) Field of Classification Search
CPC ................ B65G 1/1371; B65G 1/0485; G06K 7/10366; G06K 7/1417; G06K 7/1413; G06Q 30/014; G06Q 10/0875; G06Q 10/0833
USPC ........ 700/215, 216, 236, 244; 235/381, 385, 235/375
See application file for complete search history.

(56) References Cited

U.S. PATENT DOCUMENTS

| | | |
|---|---|---|
| 5,713,485 A | 2/1998 | Liff et al. |
| 6,247,610 B1 | 6/2001 | Ziesel et al. |

(Continued)

FOREIGN PATENT DOCUMENTS

| | | | | |
|---|---|---|---|---|
| CA | 2502489 C | * | 2/2014 | ........... G06F 19/322 |
| EP | 0 439 355 A2 | | 7/1991 | |

(Continued)

OTHER PUBLICATIONS

International Search Report and Written Opinion dated Sep. 2, 2020 received in International Application No. PCT/US2020/035262.

(Continued)

*Primary Examiner* — Edwyn Labaze

(57) ABSTRACT

The present disclosure is also directed to a system for managing inventory within a dispenser that is configured to maintain a known inventory and is configured to transmit inventory values from the dispenser so that other users can review the inventory values. Also, the dispenser is configured to be accessed by users locally and through an internet connection so that the inventory can be reviewed.

26 Claims, 18 Drawing Sheets

(51) Int. Cl.
    *G06K 7/10*         (2006.01)
    *G06K 7/14*         (2006.01)
    *G06Q 10/08*       (2012.01)
    *G06Q 30/00*       (2012.01)
    *H04N 5/76*         (2006.01)
    *A61B 17/06*       (2006.01)

(56) References Cited

U.S. PATENT DOCUMENTS

| | | | |
|---|---|---|---|
| 7,228,200 B2 * | 6/2007 | Baker | G07F 11/26 |
| | | | 221/133 |
| 7,748,628 B2 | 7/2010 | Greyshock | |
| 2003/0105555 A1 | 6/2003 | Lunak et al. | |
| 2021/0312751 A1 * | 10/2021 | Xu | G07F 11/1653 |
| 2021/0374658 A1 * | 12/2021 | Chila | G06Q 10/087 |

FOREIGN PATENT DOCUMENTS

| | | |
|---|---|---|
| WO | 97/14393 A1 | 4/1997 |
| WO | 2013/067501 A1 | 5/2013 |
| WO | 2016/040593 A1 | 3/2016 |
| WO | 2016/109726 A1 | 7/2016 |

OTHER PUBLICATIONS

International Search Report and Written Opinion dated Sep. 24, 2020 received in International Application No. PCT/US2020/035239.

* cited by examiner

INVENTORY SYSTEM AND METHODS OF USING THE SAME

CROSS-REFERENCE TO RELATED APPLICATION

This application claims the benefit of and priority to U.S. Provisional Application Ser. No. 62/854,012 filed May 29, 2019, the contents of which are incorporated herein by reference.

BACKGROUND OF THE DISCLOSURE

The present disclosure relates to dispensing and inventorying of medical products, and more particularly to systems to dispense medical products, re-stock medical products, and track and control an inventory of medical products in various medical locations, such as hospitals, clinics, outpatient surgical centers, or any other location that dispenses various medical products for use during medical procedures.

In a typical hospital, many medical products are stored in a storage area, such as a closet or storage room. As one example, the storage and use of sutures is discussed. Typically, a hospital stores hundreds of different types of sutures on racks, in cabinets or in suture storage rooms. In this typical hospital, for any given surgical procedure, a surgeon will often have what is commonly referred to as a surgeon "preference card" that specifies what products (including the types of sutures) the surgeon expects to use for that procedure, and how many of each. These sutures and supplies are obtained by the circulating nurse or other hospital staff and made available and ready to use in the surgical theater. It is common practice for any such preference card to include more sutures of a given type than what is likely to be needed, and additional types of sutures than those likely to be used to account for uncertainties during the procedure, and to avoid having to send someone to physically retrieve additional products from the storage area during surgery should the need arise.

In current practice, surgeon preference cards are manually kept, and still often exist in physical card format as opposed to electronically. They are not updated regularly, and not updated each time a surgical procedure is performed to more accurately reflect what was actually used versus what was requested for that surgery. Thus, any errors and inefficiencies in supply are repeated over and over again for a given surgeon each time he/she performs surgery. Further, the hospital has no way of tracking these errors and inefficiencies at all, let alone relative to a particular surgeon. Preference card change management is not solely owned by the surgeon, nursing or materials management. Therefore, it leads to unsuccessful change management and remediation of surgeon preference cards. Service providers have built businesses on the remediation of surgeon preference cards, but their services are expensive and not done on a consistent basis. Procedural standardization of surgical products is a growing trend in healthcare to control costs.

After a surgery is complete, all non-used sutures are to be properly restocked in their respective original storage bins and/or boxes in the storage closet. In reality, however, non-used sutures are often simply placed in a general overflow box in a storage room or thrown away. The job of restocking from a general overflow box (or otherwise) is a very time intensive process. For each individual suture package that must be restocked, the responsible individual must match the identifying information on that package with the identification on the proper box in the storage room. As indicated previously, these storage rooms may contain up to hundreds of similarly sized and shaped suture boxes. The current process is so manually intensive and time consuming, that some larger hospitals have resorted to hiring full time employees just to restock and manage sutures.

This typical system leads to waste of sutures due to improper disposal or lack of restocking, and a higher incidence of product loss due to products passing their expiration dates. This typical system also does not track who is actually removing what type of suture or quantity of sutures from the storage closet, or if any unused sutures are actually ever restocked.

Further, storage of sutures within a typical hospital leads to waste. Because hospitals typically do not have a system to accurately and timely keep track of inventory, often either too many sutures are stored-leading to waste due to expiration of those sutures, or too few sutures are stored-leading to use of alternative sutures which may not be optimal for the specific procedure.

Also, restocking of inventory is a manual, time-consuming process, which typically includes a lag time of several days to account for shipping times, actual time for a person to manually restock, etc. Nurses and materials management staff usually split the responsibility of restocking surgical product. It is estimated that it takes hospital staff over 20 hours a week to manage and restock suture products in the hospital. In 2016, the Association of Perioperative Registered Nurses reported that the national average base compensation was $70,300. Therefore, it is estimated that it costs hospital employers over $35,000 to have their operating room nurses restock and manage their suture inventory.

Although the examples discussed above refer to sutures, any medical product can be included in as these typical examples.

Manual and automated dispensing machines are known and utilized for dispensing a wide variety of items ranging from snacks and hot meals to health-related items such as certain over-the-counter medications. The vast majority of these dispensing machines are vending machines that are utilized as point of sale devices. While dispensing and vending machines are utilized in many areas, they are not widely used in the health care market.

In the field of surgery, for example, surgeons and other medical professionals rely on access to rooms of inventory having boxes of inventory manually stocked by themselves and sales representatives of the medical product manufacturers. These rooms require manual inventory control and simply hold the medical product.

There is a need to develop an improved system for stocking the medical products manually. Typically, different stock keeping units, or SKUs, need to be segregated by attributes such as diameter of suture, length of suture, color of suture, suture material (non-absorbable and absorbable), needle type, etc. As one example, one surgical suture manufacturer, Ethicon, Inc. of Somerville, N.J., has thousands of suture SKUs for various surgical procedures and other medical needs. This could translate to thousands of different suture boxes on the shelves in a larger hospital supply room. Product identification on each of the boxes is relatively small, and must be read carefully to select the appropriate sutures listed on a surgeon preference card for a given procedure and must also be read carefully in order to restock unused sutures properly. Given the manual nature of the current process, there are significant efforts in selection and restocking and inventory tracking. As indicated previously, it is estimated that a typical medium sized hospital may lose tens of thousands of dollars per year due directly to inefficiencies in the system.

As such, a need exists for better system for dispensing and restocking of sutures or other medical devices or supplies, and for otherwise more accurately and efficiently tracking inventory of such products.

Embodiments of the present disclosure provide devices and methods that address the above clinical needs.

SUMMARY OF THE DISCLOSURE

The present disclosure is directed to systems and dispensing systems.

The present disclosure is also directed to a system for managing inventory within a dispenser that is configured to maintain a known inventory and is configured to transmit inventory values from the dispenser so that other users can review the inventory values. Also, the dispenser is configured to be accessed by users locally and through an internet connection so that the inventory can be reviewed.

BRIEF DESCRIPTION OF THE DRAWINGS

The present disclosure will be better understood by reference to the following drawings, which are provided as illustrative of certain embodiments of the subject application, and not meant to limit the scope of the present disclosure.

DETAILED DESCRIPTION OF THE DISCLOSURE

Figure 1:
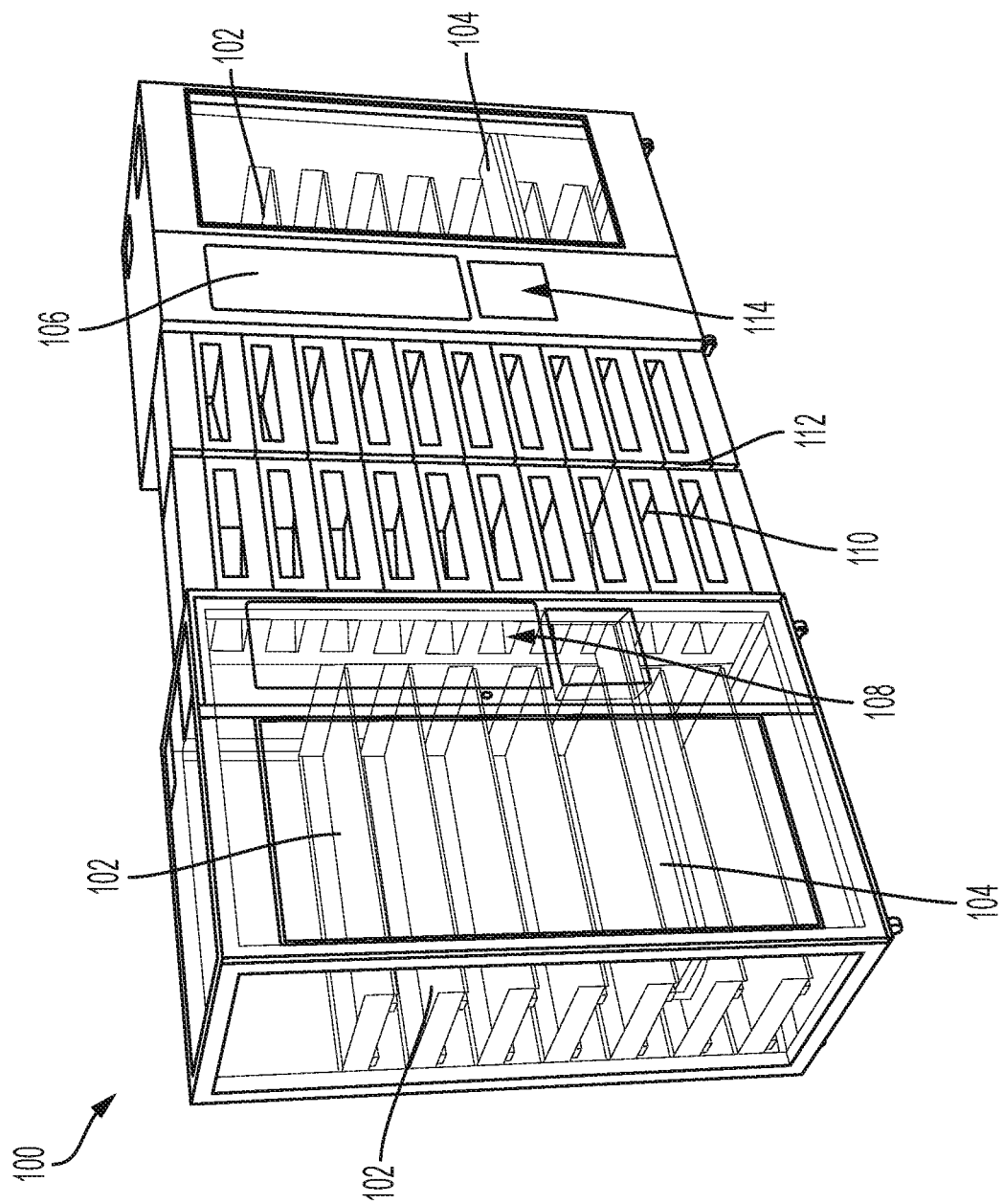
FIG. 1 is an illustration of an embodiment of a dispenser.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one embodiment", "certain embodiments", some embodiments" or "an embodiment", indicate that the embodiment(s) described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, is present on a second element, wherein intervening elements interface between the first element and the second element. The term "direct contact" or "attached to" means that a first element, and a second element, are connected without any intermediary element at the interface of the two elements.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

All measurements and/or dimensions shown in the following figures are for exemplary purposes only. In other embodiments, each of these measurements and/or dimensions can be altered in any suitable way. Further, each described component below can be formed of any suitable material, such as plastic including materials, metal including materials, carbon including materials, rubber including materials, glass including materials, etc. and combinations thereof.

As used herein, the term "medical product" refers to products such as sutures, clips, staples, fasteners, implants, hemostats (absorbable), orthopaedic pins, screws, rods, plates, staple reloads, dressings, pacing wires, an endoscope, a clamp, a saw, bone wax, drains, connectors, adapters, tubing, topical skin adhesives, etc. that can be stored in a dispenser. The dispenser is further described below, but can refer to any device that is configured to store one or more medical products, dispense and/or allow access to that medical product, maintain and/or provide an inventory of stored products, and can accept unused medical products back into a storage compartment of the dispenser.

The present disclosure is directed to dispensing systems, and systems for controlling the inventory of various medical products. One embodiment of one dispenser is shown in FIG. 1. Dispenser 100 includes several shelves 102 that are configured to hold various medical products (not shown in this figure) of various sizes and shapes. To dispense the medical product, the medical product can be moved from one of the shelves by way of a distribution mechanism (discussed below) and contact a conveyer belt 104. Although not shown, the conveyer belt 104 can move vertically within the dispenser 100, depending on which shelf 102 the medical product is on, thus reducing the distance the medical product drops while being removed from the shelf 102.

The specific medical product to be dispensed can be selected through a user's interaction with a graphical user interface 106, which can list all medical products within the dispenser 100, or can provide an illustration of all medical products within the dispenser 100, so that a user can select the desired medical product. Alternatively, the dispenser 100 can receive a transmitted request to dispense a specific medical product through an internet connection. This transmitted request can come from any other user or device that is configured to transmit request through the internet connected dispenser 100.

After the medical product contacts the conveyor belt 104, the conveyer belt 104 moves the medical product through an opening 108, and onto a dispensing shelf 110. A user can then access the medical product by opening the door 112. The doors 112 can be unlocked at all times, or, the doors 112 are first locked but can be accessed by an authorized user who authenticates their authorization by presenting an access card to the dispenser to be scanned and/or entering an access code on the graphical user interface 106. Upon authorization an unlocking mechanism within the dispenser 100 could allow for the door 112 to be manually accessed. In other embodiments, the unlocking mechanism within the dispenser 100 could cause the door 112 to be mechanically opened through a suitable mechanism, such as a pneumatic piston.

To add medical products to the dispenser, through a restocking process, a user can place a medical product in restock opening 114. As the medical product enters the restock opening, the dispenser 100 can scan the medical product through the use of a reader (such as a bar code reader, a QR code reader, a Radio Frequency Identification (RFID) reader, etc.) to read and record the restocked medical product, and store within the dispenser 100 relevant information regarding the medical product, such as a Stock Keeping Unit (SKU), the expiration of the medical product, the number of products within the package of medical product, etc. This information can be stored within the dispenser 100 and/or an external database through a communication with the dispenser 100.

Also, other users may have access to the inventory of the dispenser 100 by querying the dispenser 100 itself or accessing the inventory information saved on the external database. Thus, usage of medical products can be tracked by the identification of the accessing user, and can track inventory of the dispenser 100 by SKU or other suitable tracking method.

Further, at any time, the dispenser 100 can receive inventory information that, for example, a medical product has been recalled or is expired. The dispenser 100 could then display such data on the graphical user interface 106, or an accessing user can be notified of such information. The amount of medical product that is expired and therefore wasted, can be transmitted to the external database to affect future decisions of restocking the same or similar medical product to the dispenser 100.

Dispenser 100 has an internal computer (or can receive data from an external computer) to store inventory levels over time as medical products are dispensed and restocked.

Figure 2:
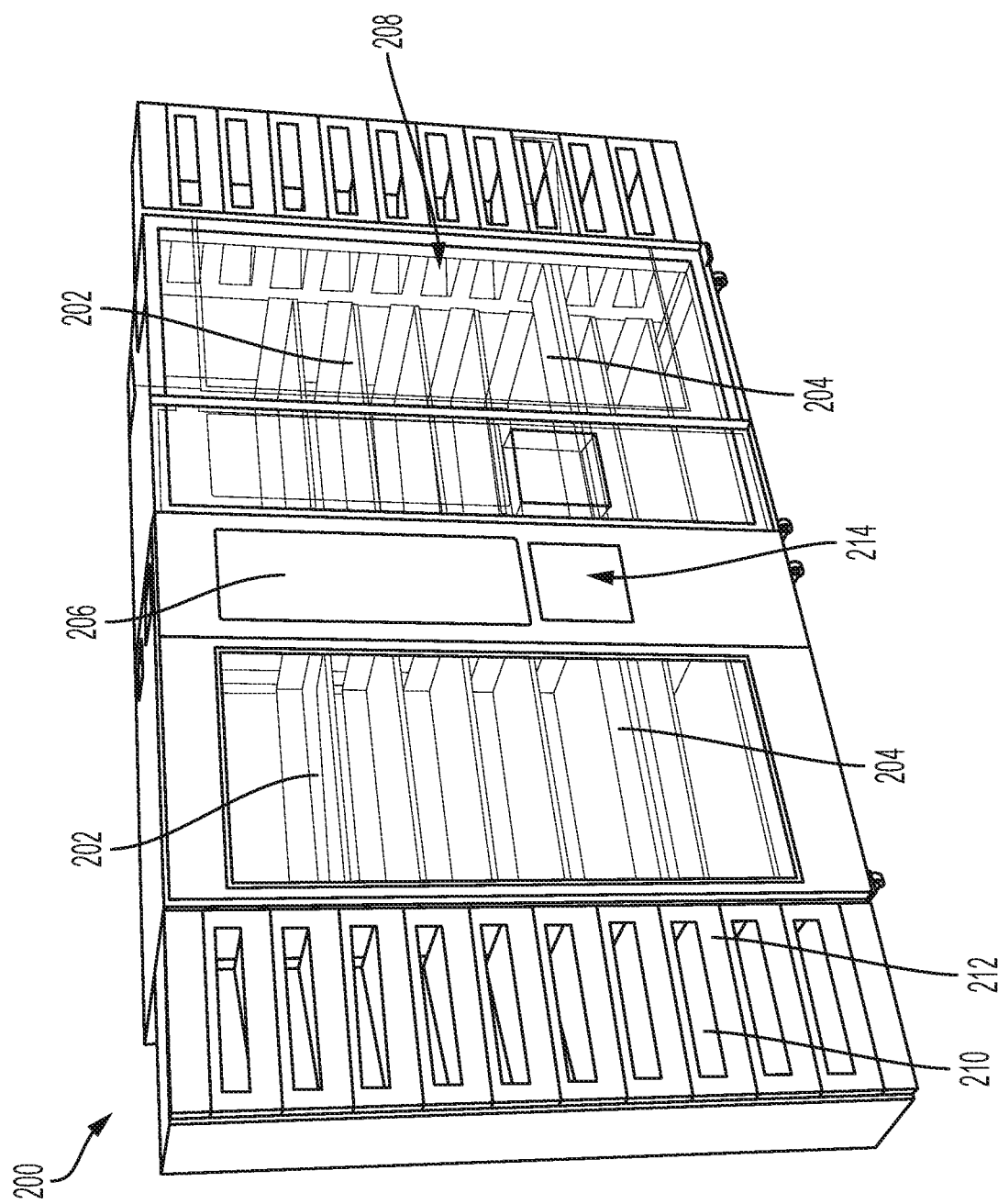
FIG. 2 is an illustration of an embodiment of a dispenser.

Another embodiment of a dispenser is shown in FIG. 2. Dispenser 200 operates similarly to dispenser 100, but is structurally different.

Dispenser 200 includes several shelves 202 that are configured to hold various medical products (not shown in this figure) of various sizes and shapes. To dispense the medical product, the medical product can be moved from one of the shelves by way of a distribution mechanism (discussed below) and contact a conveyer belt 204. Although not shown, the conveyer belt 204 can move vertically within the dispenser 200, depending on which shelf 202 the medical product is on, thus reducing the distance the medical product drops while being removed from the shelf 202.

The specific medical product to be dispensed can be selected through a user's interaction with a graphical user interface 206, which can list all medical products within the dispenser 200, or can provide an illustration of all medical products within the dispenser 200, so that a user can select the desired medical product. Alternatively, the dispenser 200 can receive a transmitted request to dispense a specific medical product through an internet connection. This transmitted request can come from any other user or device that is configured to transmit request through the internet connected dispenser 200.

After the medical product contacts the conveyor belt 204, the conveyer belt 204 moves the medical product through an opening 208, and onto a dispensing shelf 210. A user can then access the medical product by opening the door 212. The doors 212 can be unlocked at all times, or, the doors 212 are first locked but can be accessed by an authorized user who authenticates their authorization by presenting an access card to the dispenser to be scanned and/or entering an access code on the graphical user interface 206. Upon authorization an unlocking mechanism within the dispenser 200 could allow for the door 212 to be manually accessed. In other embodiments, the unlocking mechanism within the dispenser 200 could cause the door 212 to be mechanically opened through a suitable mechanism, such as a pneumatic piston.

To add medical products to the dispenser, through a restocking process, a user can place a medical product in restock opening 214. As the medical product enters the restock opening, the dispenser 200 can scan the medical product through the use of a reader (such as a bar code reader, a QR code reader, a Radio Frequency Identification (RHD) reader, etc.) to read and record the restocked medical product, and store within the dispenser 200 relevant information regarding the medical product, such as a Stock Keeping Unit (SKU), the expiration of the medical product, the number of products within the package of medical product, etc. This information can be stored within the dispenser 200 and/or an external database through a communication with the dispenser 200.

Figure 3:
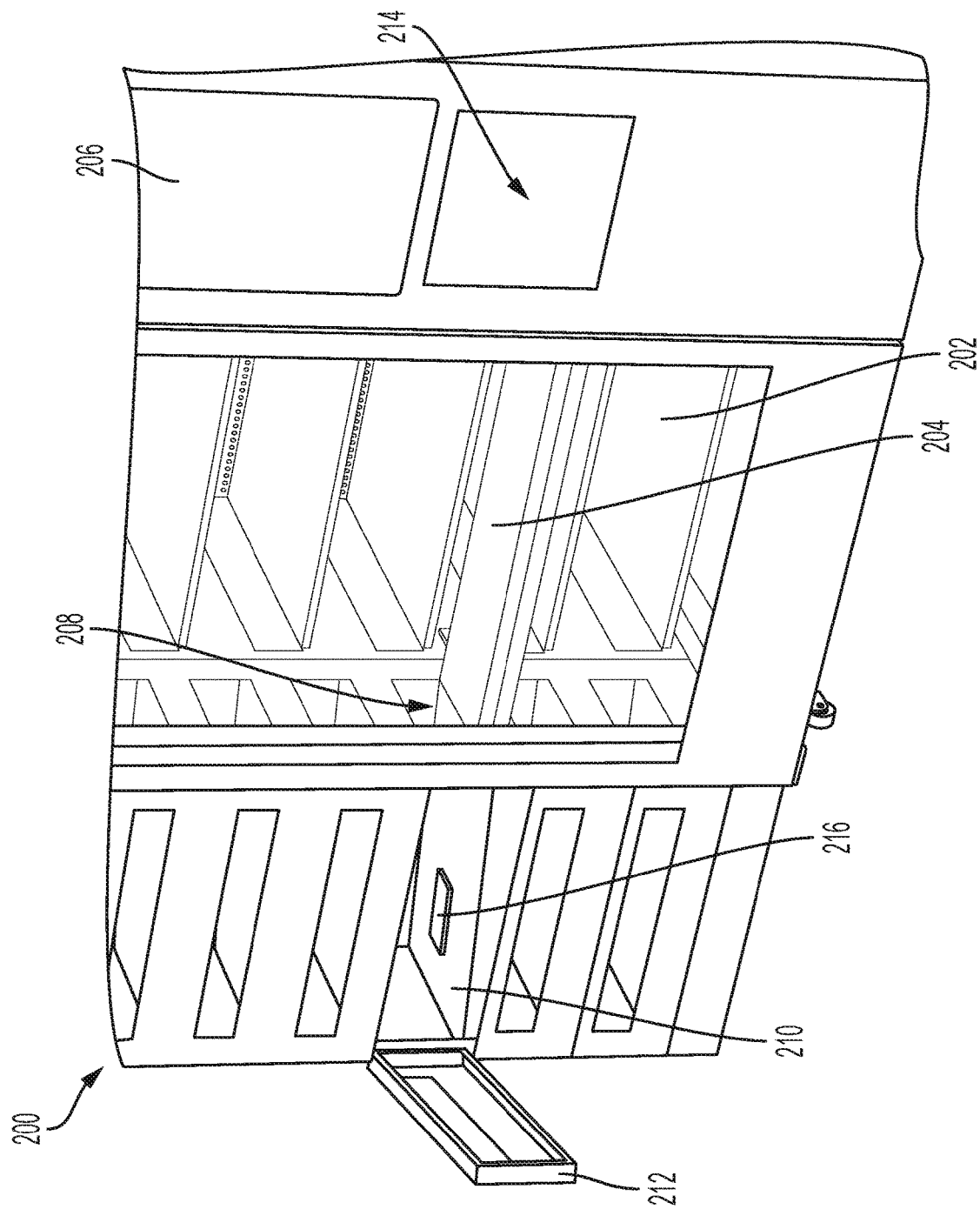
FIG. 3 is a magnified view of a portion of the dispenser of FIG. 2.

A magnified view of a portion of dispenser 200 is shown in FIG. 3. In FIG. 3, a medical product 216 has been moved from one of the shelves 202, contacted the conveyer belt 204, caused to move by the conveyer belt 204 through the opening 208 and onto the dispensing shelf 210. In this view the door 212 is in an open configuration, allowing a user to reach within the dispenser 200 and remove the medical product 216 from the dispensing shelf 210.

Figure 4:
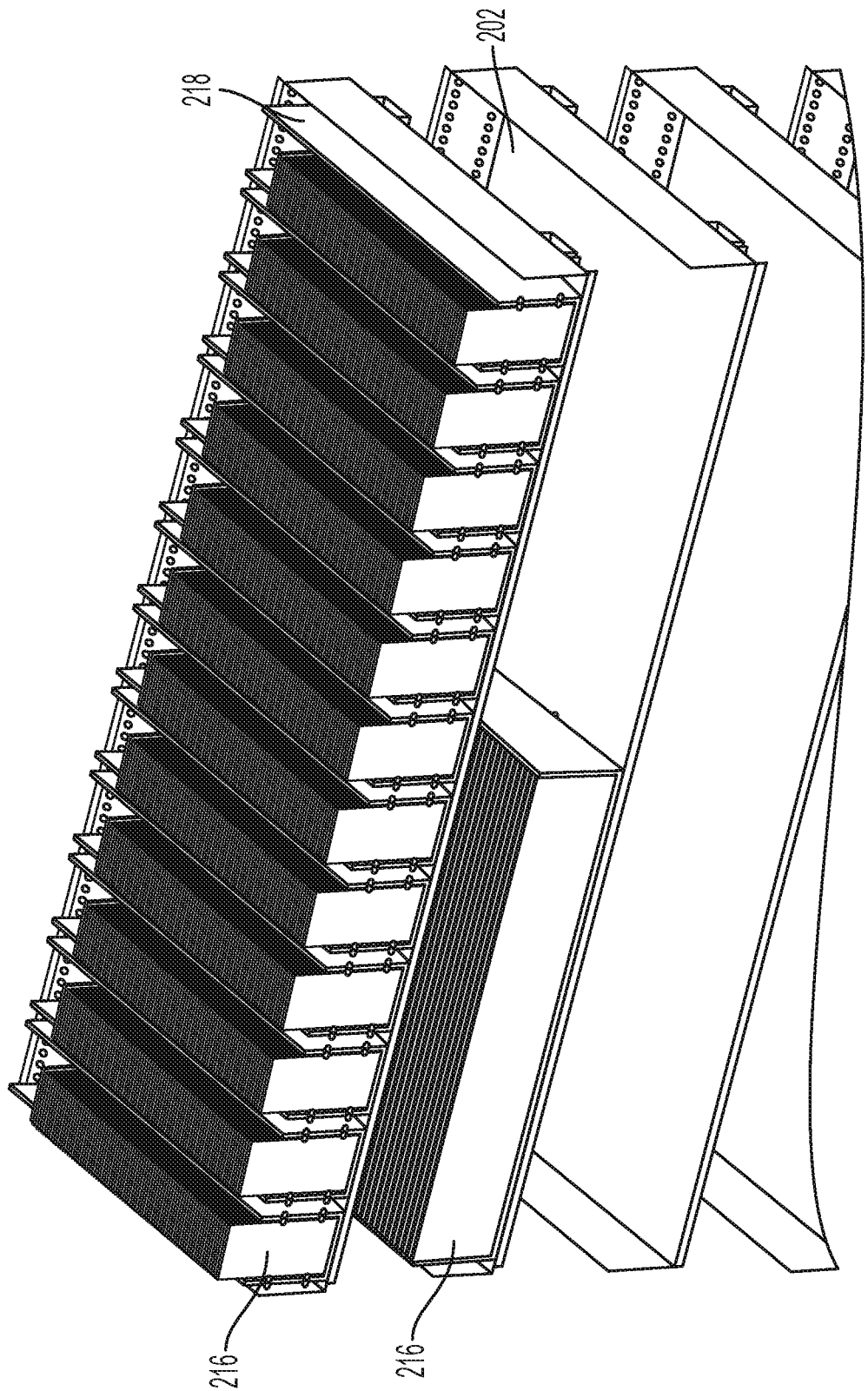
FIG. 4 is a view of a plurality of stored medical products.

A view of an internal space of the dispenser 200 (or for the dispenser 100) is shown in FIG. 4. FIG. 4 illustrates shelves 202 that contain a plurality of medical products 216. As can be seen multiple different sizes of medical products can be stored on the shelves 202 within various sized trays 218. The trays 218 can be configured to maintain the medical products 216 in any suitable orientation and can maintain 1, 5, 10, 15, 20, 30, 40 or more individual medical products 216 within the tray 218. The tray 218 can be resting on shelf 202 in a designated location and/or the tray 218 can be releasably connected to the shelf 202 in any suitable way.

Figure 5:
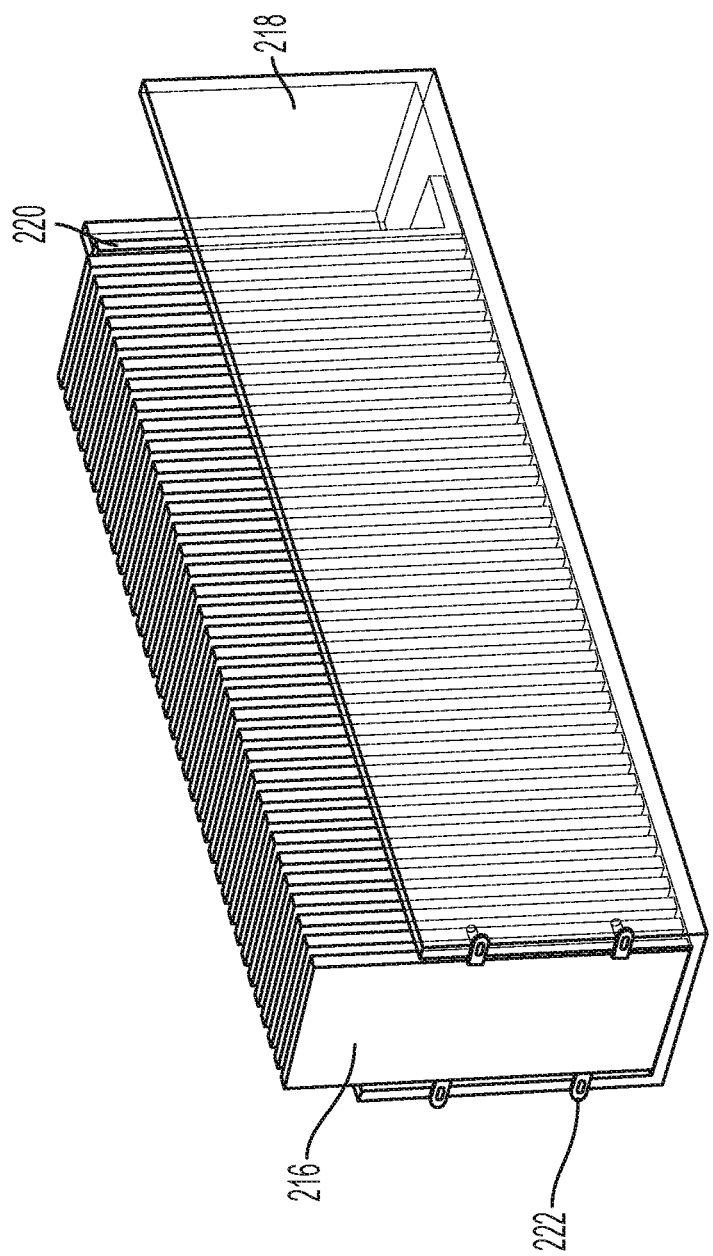
FIG. 5 is a view of a plurality of stored medical products.

A more detailed view of the tray 218 is shown in FIG. 5 (without the shelf 202), with a portion of the tray 218 being translucent for illustrative purposes. In the embodiment of the tray 218 shown in FIG. 5, a plurality of medical products 216 are stored vertically between the walls of the tray 218 and between an urging component 220 and one or more securing tabs 222. The securing tabs 222 are to be oriented towards the front of the shelf 202, which is closer to conveyor (204 of FIG. 2).

The urging component 220 can provide a force towards the retaining tab 222 through gravity and/or by a spring force. In this embodiment of the tray 218, four retaining tabs 222 are shown, which prevent the medical prevent 216 from falling out of the tray 218, but also allowing removal of the medical product 216 by way of a distribution mechanism, discussed below.

Figure 6:
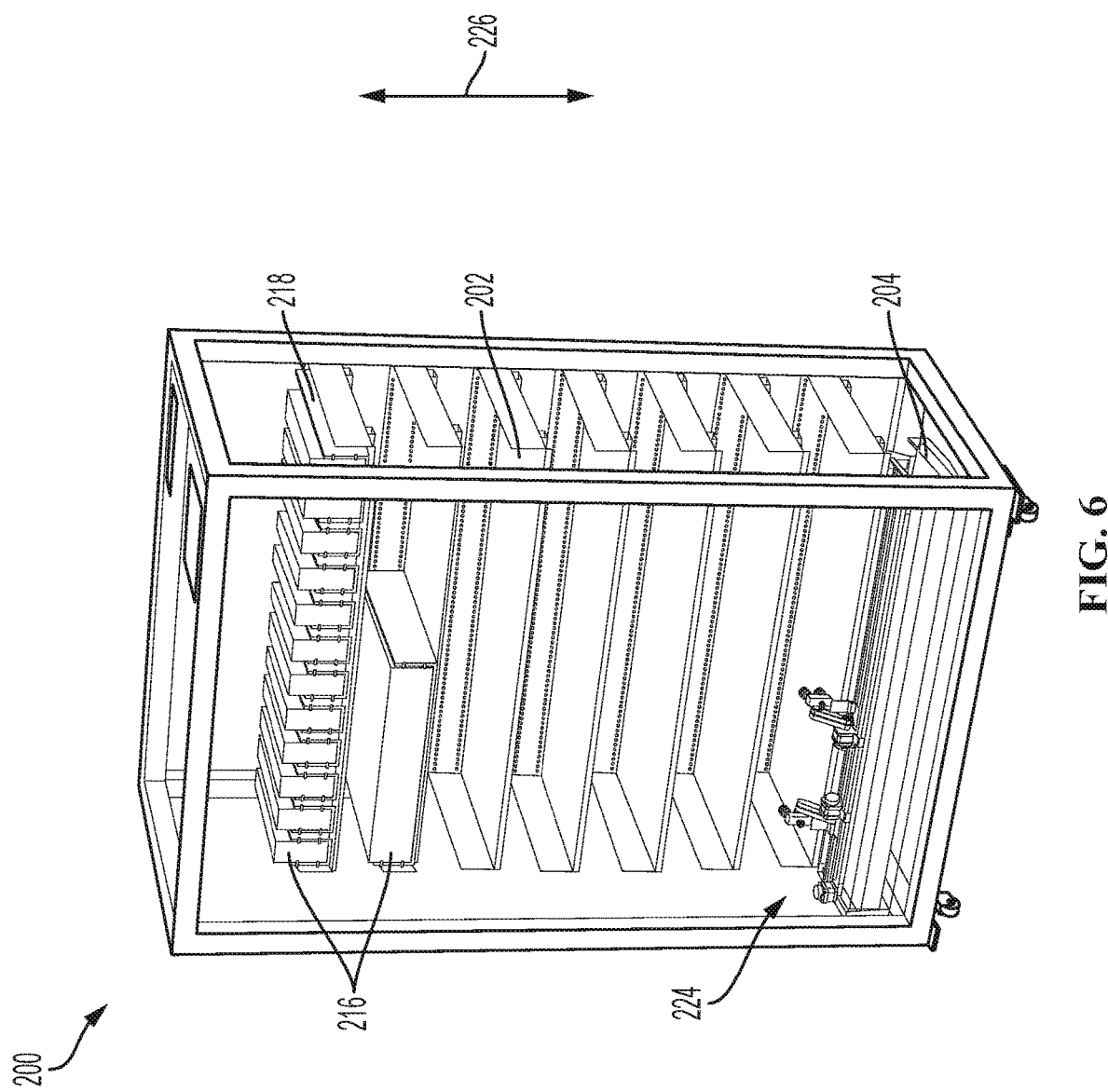
FIG. 6 is a view of a plurality of stored medical products within a dispenser.

A distribution mechanism 224 is illustrated in FIG. 6, which shows an interior of a dispenser 200, along with shelves 202, a portion of which are holding trays 218, which themselves are holding medical products. For illustrative purposes several shelves 202 are shown as not holding any trays 218, but in other embodiments, all space, or a majority of space, on the shelves 202 can hold trays 218 of various sizes.

The distribution mechanism 224, which includes the conveyor belt 204, can move vertically within the dispenser 200, so that the conveyor 204 is brought to a relatively close position to the shelf 202 the desired medical product 216 is on. In this embodiment, the distribution mechanism 224 is shown as being in a position to retrieve a medical product from the lowest shelf 202. In other embodiments, the distribution mechanism would rise vertically through any suitable mechanism in the direction of arrow 226, to be in a position to retrieve a medical product from any of the other (in this embodiment six) shelves 202.

Figure 7:
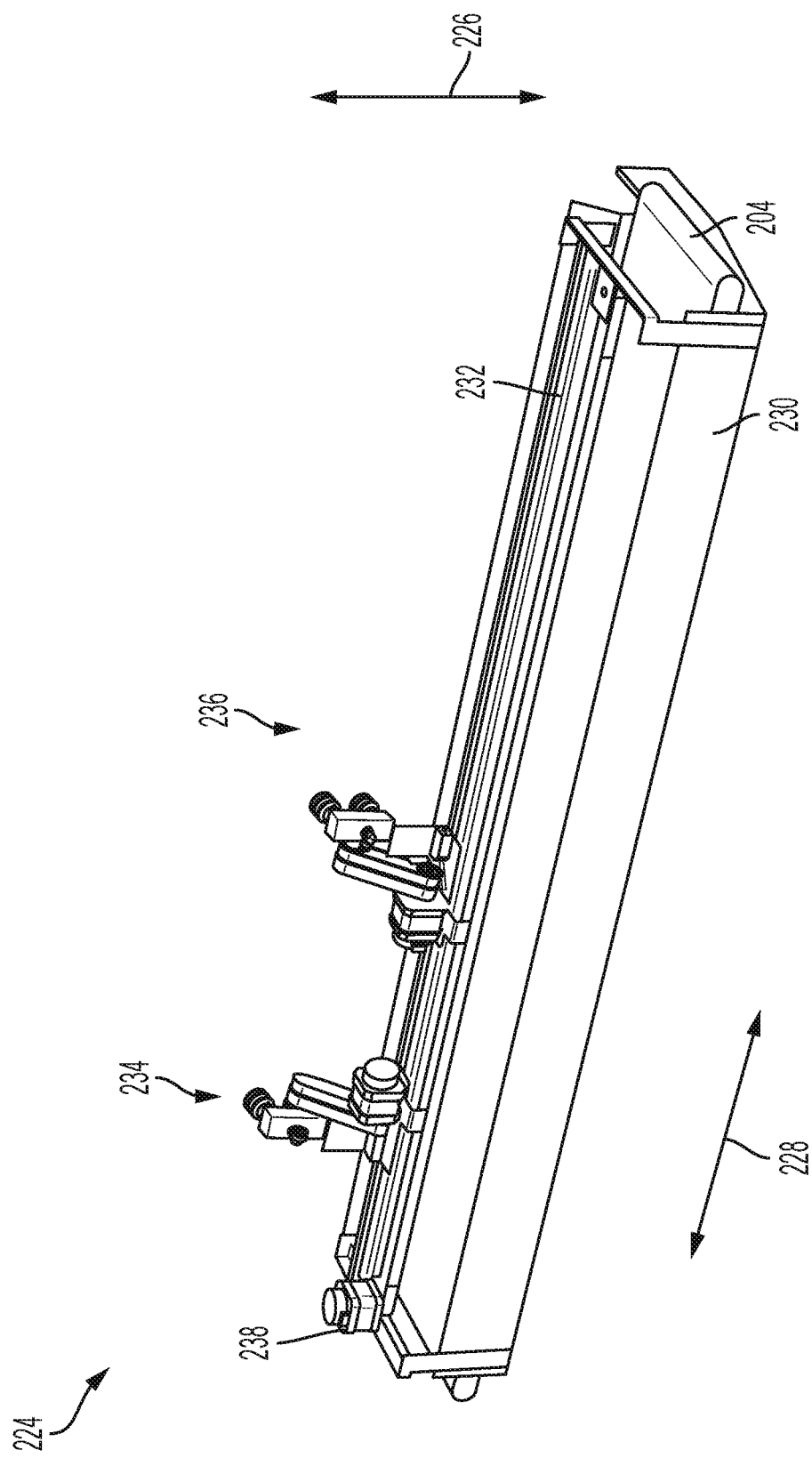
FIG. 7 is a view of a distribution mechanism.

A more detailed view of the distribution mechanism 224 is shown in FIG. 7. The entire distribution mechanism 224 shown in FIG. 7 is configured to move vertically within the dispenser in the direction of arrow 226.

In FIG. 7, the conveyer belt 204 can be caused to move in either direction of arrow 228 by a motor and rollers (not shown). The conveyer belt 204 is sits within a frame 230 that supports a guide rail 232. The guide rail 232 is configured to support a left arm mechanism 234 and a right arm mechanism 236. In this embodiment two similar arm mechanisms are shown in FIG. 7, but, in other embodiments a one arm mechanism, three arm mechanisms, or more may be included, with each arm mechanism being similar or different from each other included arm mechanism.

One or both of the left arm mechanism 234 and the right arm mechanism 236 can move along the guide rail 232, in either direction of arrow 228, through a force provided by a motor 238. A more detailed view of the right arm mechanism 236 is shown in FIG. 7. Although the first arm mechanism 236 is shown in more detail, the left arm mechanism 234 includes the same components, just arranged differently.

In FIG. 7, an arm mechanism frame 240 supports the other elements of the right arm mechanism 236. The arm mechanism frame 240 supports an arm motor 242, which has an axle (not shown) that is caused to rotate clockwise or counter-clockwise. The axle of the arm motor 242 subsequently causes motor pivot 243 to rotate and arm belt 244 around motor pivot 243 and arm pivot 250. The movement of motor pivot 243 and the arm belt 244 subsequently causes support arm 246 to rotate in the direction of arrow 245.

An arm axle 251 extends through the arm pivot and supports suction frame 252. Suction frame 252 supports, in this embodiment two suction heads 254 that receive a suction pressure through a suction force received through a gas fitting 256 (connecting hoses not shown). In this embodiment two suction heads 254 are supported by suction frame 252, however in other embodiments, one suction head, three suction heads, or more, may be supported by suction frame 252. The suction heads 254 are made of a comparatively compliant material, which can flex and which can include an opening for delivery of a suction pressure to a portion of a medical product (shown in later figures).

Also supported by the arm mechanism frame 240 is a sensor 258, which as discussed below, can be used to determine a horizontal location on the shelf. In this embodiment, sensor 258 is a laser sensor, but in other embodiments, any other suitable sensor, including an optical sensor, can be included.

Figure 9B:
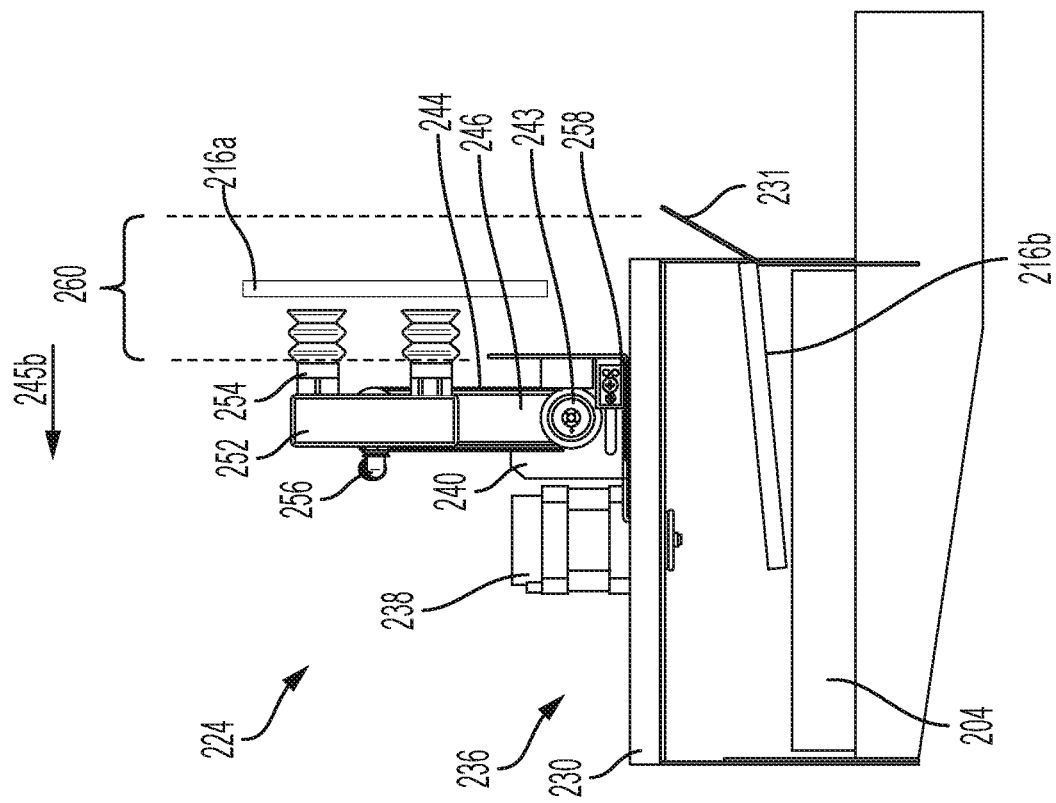
FIGS. 9A and 9B are views of the arm of the distribution mechanism.
Figure 9A:
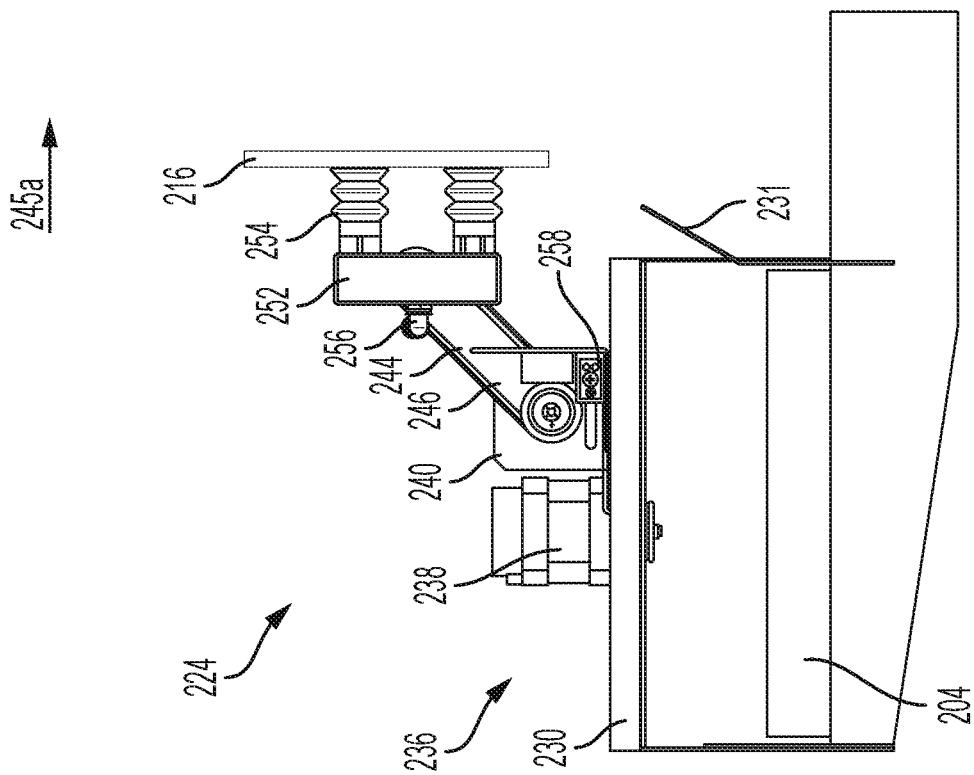

Operation of the right arm mechanism 236 is shown in FIGS. 9A and 9B. Both FIGS. 9A and 9B are right hand side views of the distribution mechanism 224.

Figure 8:
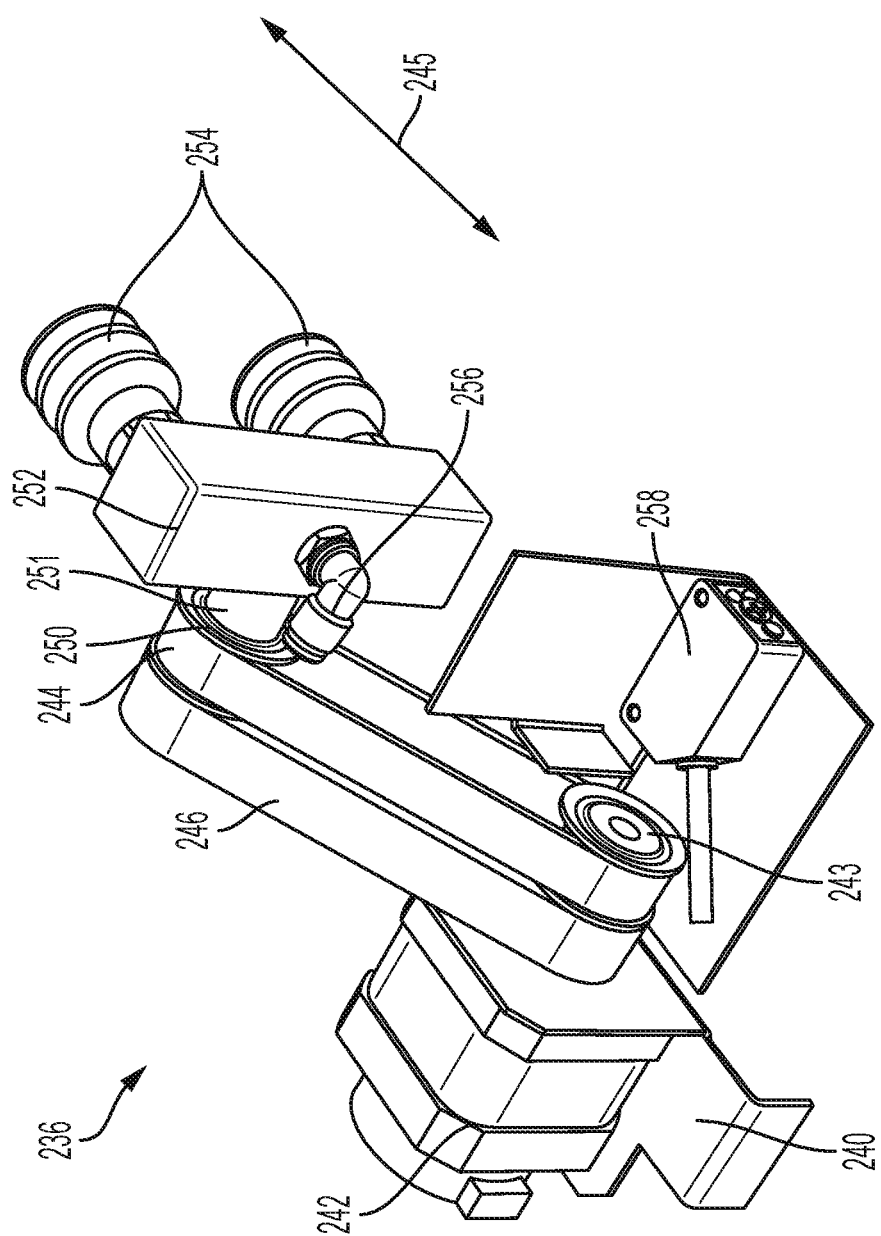
FIG. 8 is a view of an arm of the distribution mechanism.

In FIG. 9A, the right arm mechanism 236 is in a picking position. The motor 242 (of FIG. 8) has rotated clockwise and caused the suction frame 252 to move in the direction of arrow 245a, so that a front surface of the suction heads 254 contact a medical product 216 (although not shown, the medical product 216 would be stored in a frame, as shown in FIG. 6).

A suction pressure is received through the gas fitting 256, and a sufficient suction pressure is formed between the suction heads 254 and the medical product 216 so that the medical product 216 is removed from the frame.

In FIG. 9B, the right arm mechanism 236 is in a dropping position (which when no medical product 216 is being picked, also a resting position). The motor 242 (of FIG. 8) has rotated counter-clockwise and caused the suction frame 252 to move in the direction of arrow 245b until the medical product 216 is in a drop zone 260, illustrated as two imaginary lines in FIG. 9B. During movement from FIG. 9A to 9B, a suction pressure is continually supplied to suction heads 254.

Once the medical product 216a is in the drop zone 260, as it is in FIG. 9B, the suction pressure being supplied to suction heads 254 is stopped, and the medical product 216a, by gravity, falls vertically down, possibly contacting a flared frame portion 231, and lands on the conveyor belt 204, so that the medical product 216b is in any suitable orientation on the conveyor belt 204. The medical product 216 b can then be moved by the conveyor belt 204 in either direction of arrow 228 of FIG. 7 and subsequently removed from the dispenser 200. Since the dispenser 200 would effect selection of the specific medical product 216, the inventory of the dispenser 200 can be updated to reflect the removal of the medical product 216 after the user has accessed the medical product 216.

Figure 10:
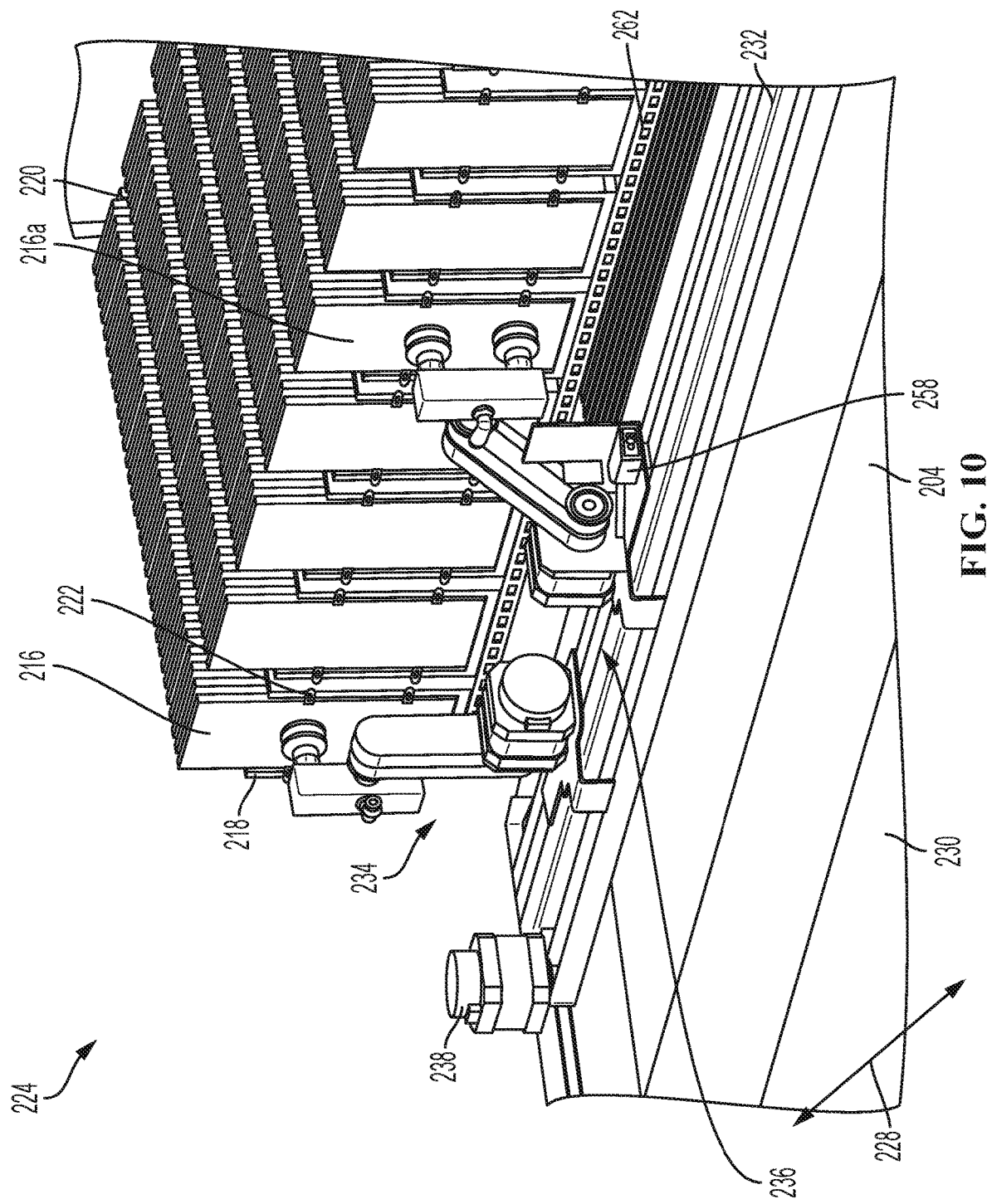
FIG. 10 is a view of the distribution mechanism interacting with a plurality of stored medical products within the dispenser.

FIG. 10 illustrates the distribution mechanism 224 being in the highest vertical position in the dispenser 200 of FIG. 6. In this figure, the left arm mechanism 234 is in the resting position, while the right art mechanism 236 is in the picking position. The right arm mechanism 236 has been moved along the guide rail 232 to the appropriate location, so that the suction heads contact medical product 216a, as opposed to other medical products. To ensure that the suction heads are sufficiently aligned with the medical product 216a, the sensor 258 emits a signal and counts the number of notches 262 in the shelf 202 as the right arm mechanism 236 moves in the direction of arrow 228. Alternatively, the sensor 258 can determine the horizontal location on the shelf in any other suitable way, such as through an optical code, or various shaped notches, etc.

Figure 11:
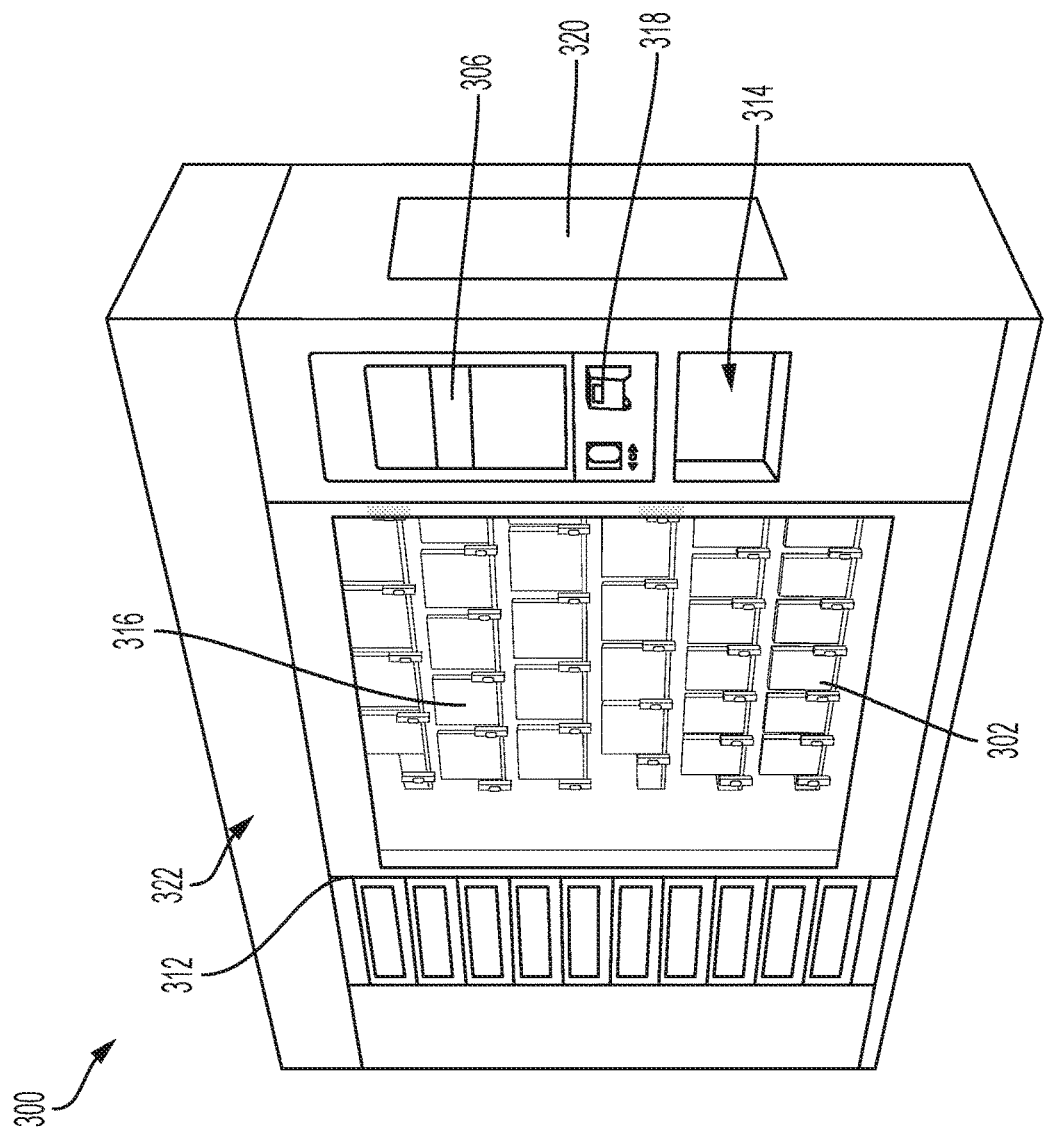
FIG. 11 is an illustration of an embodiment of a dispenser.

Another embodiment of a dispenser is shown in FIG. 11. Dispenser 300 operates in a similar way to the dispensers discussed above. Dispenser 300 includes a plurality of medical products 316 on shelves 302, which can be accessed through doors 312 and/or through a restock/delivery opening 314.

In this embodiment of dispenser 300, as well as dispensers 100 and 200, instead of relying on mechanisms within the dispenser itself, a stocking user could access one of the doors 312, place one or more medical products 316 within the door. The dispenser 300 could first scan these medical products being added with a reader and/or the stocking user could interact with the graphical user interface 306 to update the inventory amount of the medical product just added.

Once another user accesses the dispenser 300, that user could be notified that one or more of their requested medical products is in the stocked door 312, and the dispenser 300 could allow access to that door 312. The dispenser 300 could also cause the door 312 to pop open mechanically, and/or have a portion of the door 312 (or a space adjacent to the door 312) light up to indicate which door the user should access. Once the medical products are removed by the user, the dispenser 300 could update its own inventory values to indicate the medical product has been removed.

In this embodiment, the dispenser includes two graphical user interfaces 307, so a user can interact with the dispenser 300 in any suitable way. For example, a user can access the graphical user interface 306 by first scanning an identification card with an ID reader 318. In other embodiments the user could be identified through a fingerprint scan and/or a retinal scan by the ID reader 318.

The graphical user interface 306 can then allow the user to access what inventory of medical products are present in the dispenser 300, and request their withdrawal and/or access. The graphical user interface 306 can also show instructional videos on how to use the selected medical product, or present alternative medical products and show a comparison between the selected medical product and the possible alternative medical product. Also, the graphical user interface 306 can be used to order further stock of one or more medical products.

The graphical user interface 306 can also accept a request directly (or through receiving a transmitted request) to have specific medical products 316 within a door 312 and/or within restock/delivery opening 314 at specified time in the future.

Aesthetically, the dispenser can include an image, which may be a static image such as a poster, or a dynamic image presented on a display screen. Also, the dispenser can include signage in a signage area 322 to let users know the source of the dispenser 300 and/or the medical products 316 within the dispenser 300.

Figure 12:
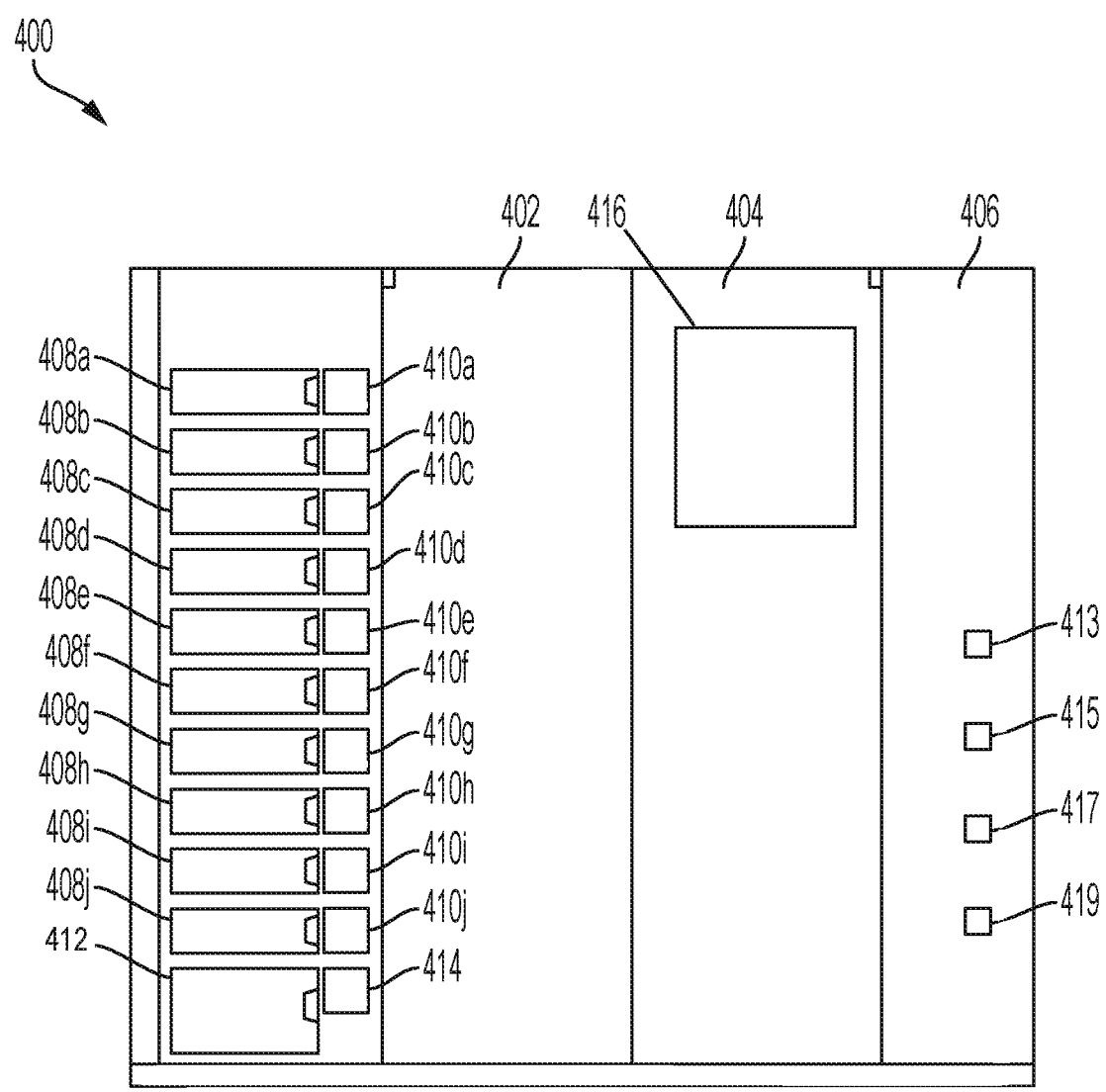
FIG. 12 is an illustration of an embodiment of a dispenser.

Another embodiment of a dispenser is shown in FIG. 12. Dispenser 400 operates similarly to dispenser 300, but is structurally different.

The dispenser 400 in FIG. 12 is illustrated with each of a left movable door 402, a right movable door 404, a return door 406, openable doors 408a-408j retrieval notification displays 410a-410j, a error door 412, an error notification display 414, and a display 416. Although FIG. 12 represents an external view of the dispenser 400, several components are within a cavity formed within dispenser 400, and will be discussed below in reference to further figures.

As noted, dispenser 400 includes several openable doors 408a-408j, which are configured to open and provide access to a dispensing area, which may be a shelf and/or a bucket that is configured to hold various medical products (not shown in this figure) of various sizes and shapes. For the dispenser 400 to dispense the medical product, the medical product can be moved from an internal storage area, down a ramp, and into a dispensing area, which may include a shelf and/or bucket, details of which will be discussed below.

Adjacent each of the openable doors 408a-408j is a retrieval notification display 410a-410j. Each of the retrieval notification displays 410a-410j can be any suitable display, such as a suitable liquid crystal display (LCD) and a light emitting diode (LED) display. Each of the retrieval notification displays 410a-410j can display various information, such as the name of the surgeon to which the medical products are to be dispensed, the type of procedure(s) that are to be performed with the dispensed medical products, a list of the medical products that are to be dispensed into the respective openable door 408a-408j, the location within the facility the medical products that are to be dispensed are scheduled to be used, and/or the time the procedure(s), for which the medical products are to be dispensed, is scheduled to begin.

Each of the retrieval notification displays 410a-410j can include a button (shown as a circle on each of the retrieval notification displays 410a-410j), which is configured to receive a response from a user. The response is selected from the group consisting of an input force from a user, an input contact from the user, and/or an input of near physical contact within a predetermined proximity. The database then determines that the medical products in the dispensing area behind one of the openable doors 408a-408j is no longer stored within the dispenser 400 and is to be removed from the available inventory of the dispenser 400.

Each button on each of the retrieval notification displays 410a-410j can include a light source that can be configured to change color amongst three different colors for example from red, to yellow, to green, upon receipt of a signal to indicate various messages, such as whether the total number of medical products of a pick list are accessible through the corresponding openable doors 408a-408j. In other examples, each button can include a light source that is configured change color amongst one (light on or off) two different colors, or four or more different colors.

For example, each button can be red (which can indicate that the corresponding openable doors 408a-408j is not in use or can indicate that not all medical products of the pick list are ready to be dispensed from the corresponding openable doors 408a-408j), each button can be green (which can indicate all medical products of the pick list are ready to be dispensed from the corresponding openable doors 408a-408j), or each button can be yellow (which can indicate that an error has occurred, or that at least one of the medial products in the dispensing are is different from the medical product of the pick list, or that some but not all medical products are ready to be dispensed from the corresponding openable doors 408a-408j).

The button can be yellow if at least one of the medial products in the dispensing area is different from the medical product of the pick list. The inclusion of a different medical product from the medical products of the pick list can occur if a medical product of the pick list is not available, but a predetermined and one or more suitable substitute medical products is present within the dispenser, and has been moved to the dispensing area. Each dispenser 400 can store internally, or can receive a signal from a database, a list of suitable substitute medical products for each medical product stored within the dispenser 400 at a point in time. This point in time can be the original replenishment of the dispenser 400, so that a plurality of medical products are stocked within the dispenser 400, or this point in time can be a time when an originally stocked medical product is replaced with a different medical product.

One of the buttons corresponding to a retrieval notification display 410a-410j can receive a response from a user. Upon receiving the response, the button allows for access to the medical product(s) that have been placed into the dispensing area behind the corresponding openable doors 408a-408j.

Receipt of the response by the button of the retrieval notification display 410a-410j is also acknowledged and stored within a local electronic storage device 413 of the dispenser 400 and/or stored within a cloud based service connected to the dispenser 400. Thus, dispenser 400 can alter the color of the button of the retrieval notification display 410a-410j, and if further medical products are to be dispensed, begin to move medical product(s) stored within the dispenser 400 to the shelf and/or bucket behind the corresponding openable doors 408a-408j.

Dispenser 400 also includes the error door 412 covering a single error area, and the error notification display 414. Although in FIG. 12 the error door 412 and the error notification display 414 are illustrated as being vertically below all of the openable doors 408a-408j and the retrieval notification display 410a-410j, in other embodiments, the error door 412 and the error notification display 414 can be in any location on the dispenser 400. The single error area is configured to hold at least one medical product.

Medical products from within the dispenser 400 can be moved to the error area behind the error door 412 for one of several reasons. For example, medical product(s) can be placed in the error area since they are, upon a scanning feature described below, acknowledged by the dispenser 400 as being expired (or within a threshold amount of time before expiration). As another example, upon return of medical product(s) that have previously been dispensed from dispenser 400, those returned medical product(s) may be damaged, or may be incapable of being scanned with a reader (as discussed below). As another example, upon return of medical product(s) that have previously been dispensed from dispenser 400, those returned medical product(s) may be identified as not being the same as any other medical products within the dispenser 400. As another example, the dispenser 400 can receive data indicating that a certain type of medical product(s) have been recalled, upon receipt of such data, the dispenser 400 can then cause those medical product(s) to be moved from storage within the dispenser 400 into the error area behind the error door 412.

In each example above of a medical product being moved to the error area, a first communication interface 419 of the dispenser 400 can be configured to transmit to a cloud based service and/or database outside the dispenser 400, a signal that an error is determined and/or the medical product is in the error area. Any communication interface of the present disclosure may be a wireless communication interface. In other aspects of the disclosure, a communication interface may be a wired communication interface.

Error notification display 414 can be any suitable display and can display various information, such as: the amount and/or type of medical products in the error area behind the error door 412; a notification that a threshold number of medical product(s) have been received in the error area behind the error door 412 so that a user can empty the medical product(s) received in the error area behind the error door 412; and a notification that medical product(s) are presently being moved into the error are behind the error door 412 (so that the user can wait until all medical product(s) have been moved to the error area behind the error door 412 before removing them).

Error door 412 may be opened by any user, or error notification display 414 can receive a passcode (or include a physical key slot) so that error door 412 can be opened by an authorized user.

Dispenser 400 also includes the left movable door 402, which as shown in FIG. 12 is in a closed position, but can pivot towards the openable doors 408a-408j to an open position to allow a user to sufficiently access the interior of the dispenser 400. Dispenser 400 also includes the right movable door 404, which as shown in FIG. 12 is in a closed position, but can pivot towards the return door 406 to an open position to allow a user to sufficiently access the interior of the dispenser 400. Although in this embodiment the left movable door 402 and the right movable door 404 are shown as relatively large, vertical doors, in other embodiments, only one door, or three or more doors can be included, in any size and orientation, to allow for sufficient access to the interior of the dispenser 400 to allow for restocking, etc., by a user.

Also as seen in FIG. 12, the display 416 can be a graphical user interface (GUI), and is included on a front surface of the left movable door 402, but, in other embodiments, the display 416 can be in any other suitable location on the dispenser 400.

The display 416 can be configured to receive an input contact from a user, wherein the contact is used to receive a code (such as an access code so that a user can open one or more doors of the dispenser 400), receive a selection for a video recording (so that a user can record a video message, such as a description of an error of a dispensed medical product), display received video (which can be received from a cloud based service and/or an external database), and receive signals from the electronic storage device 413 within the dispenser 400. The display 416 can also display data selected from the group consisting of a number of each of the plurality of medical products within the dispenser, a location of each of the plurality of holders, and which medical product of the plurality of medical products is stored in each of the plurality of holders.

The input from the user received by the display 416 can be a specific medical product(s) to be dispensed from dispenser 400 can be selected through a user's interaction with the display 416, which can list an inventory of all medical products within the dispenser 400, or can provide an illustration of all medical products within the dispenser 400, so that a user can select the desired medical product. Alternatively, the dispenser 400 can receive a transmitted request to dispense a specific medical product through an internet connection. This transmitted request can come from any other user or device that is configured to transmit request through the internet connected dispenser 400.

The display 416 allows a user to interact with the dispenser 400 in any suitable way. For example, a user can access the display 416 by first scanning an identification card with an ID reader 318 and/or entering a passcode.

In this embodiment the dispenser 400 also includes a speaker that is configured to provide an audio signal (such a warning signal), and/or provide an audio transmission of a recorded video message shown on the display 416.

The display 416 may also present alternative medical product(s) to those selected, and show a comparison between the selected medical product and the possible alternative medical product. Also, the display 416 can be used to order further stock of one or more medical products.

The display 416 can also accept a request directly (or through receiving a transmitted request) to have specific medical product(s) on a shelf and/or bin being the openable doors 408a-408j known by the dispenser to be vacant.

Dispenser 400 also includes the return door 406 that covers a restocking area. Although in this embodiment the return door 406 is shown as a relatively large, vertical door, in other embodiments, two or more doors can be included, in any size and orientation, to allow for users to sufficiently place unused medical product(s) within the restocking area behind the return door 406, so that the unused medical product(s) can be added to the stored inventory within the dispenser 400 as discussed below.

Figure 13:
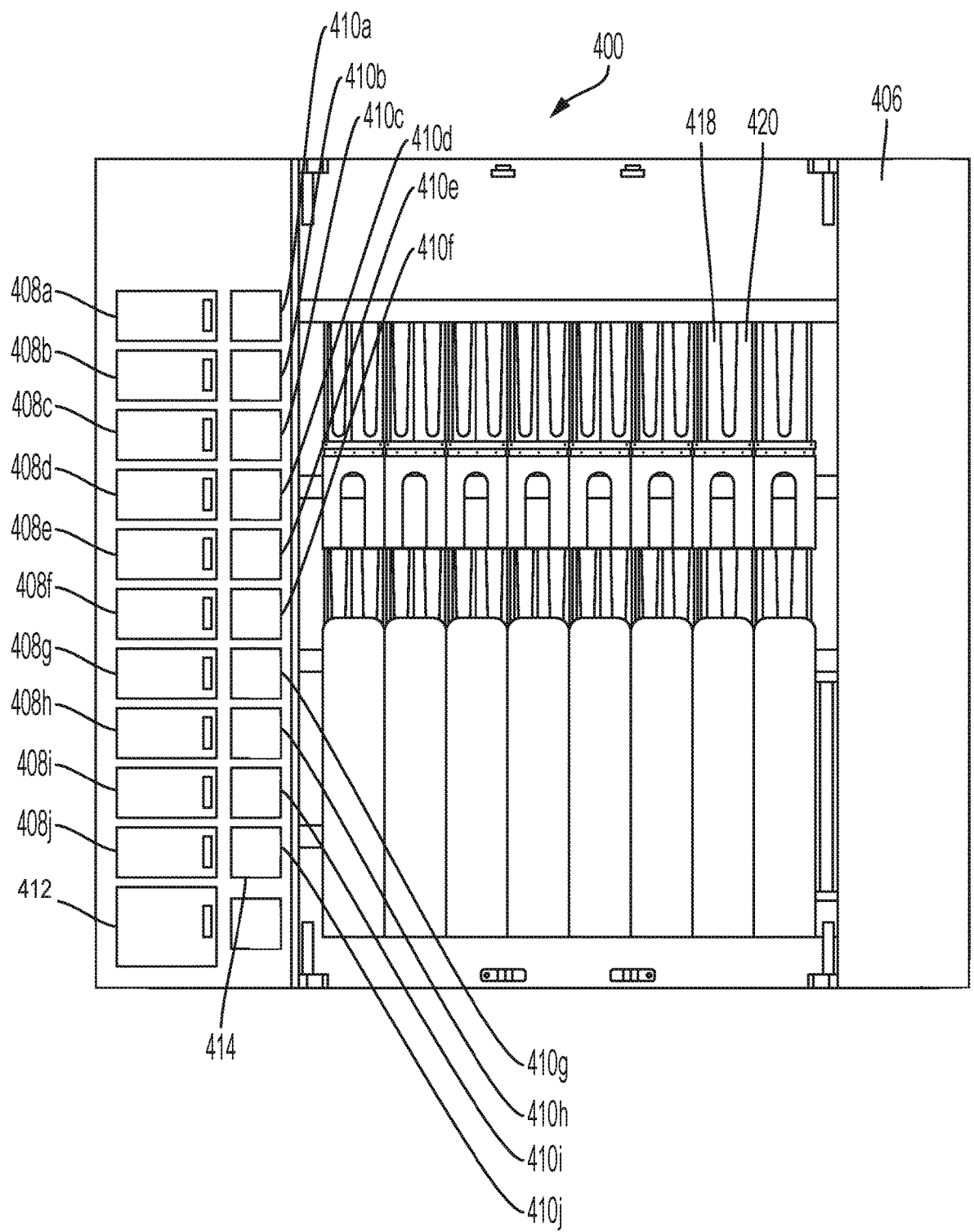
FIG. 13 is an illustration of an interior of the dispenser.

FIG. 13 is a view of dispenser 400, with left movable door 402 and right movable door 404 removed, so that a portion of the interior of dispenser 400 is visible. In this view, a holder 418 is shown, with the interior of the dispenser 400 containing a plurality of holders, each of which are configured to store one or more medical products in fixed locations within the dispenser 400. Each of the plurality of holders 418 is configured to maintain one or more medical products in a fixed location, so that a plurality of medical products can be stacked on top of each other within each of the plurality of holders 418. Each of the plurality of holders 418 can be the same size, so that the stored medical product is the same size for each holder 418, or the plurality of holders 418 can be varied sizes so that medical products of different sizes can be stored therein.

Each of the holders 418 can completely surround the circumference of each of the medical products, or one or more holders 418 can include a slot 420, so that a portion of a medical product stored within the holder 418 can be visible and/or accessible.

Figure 14:
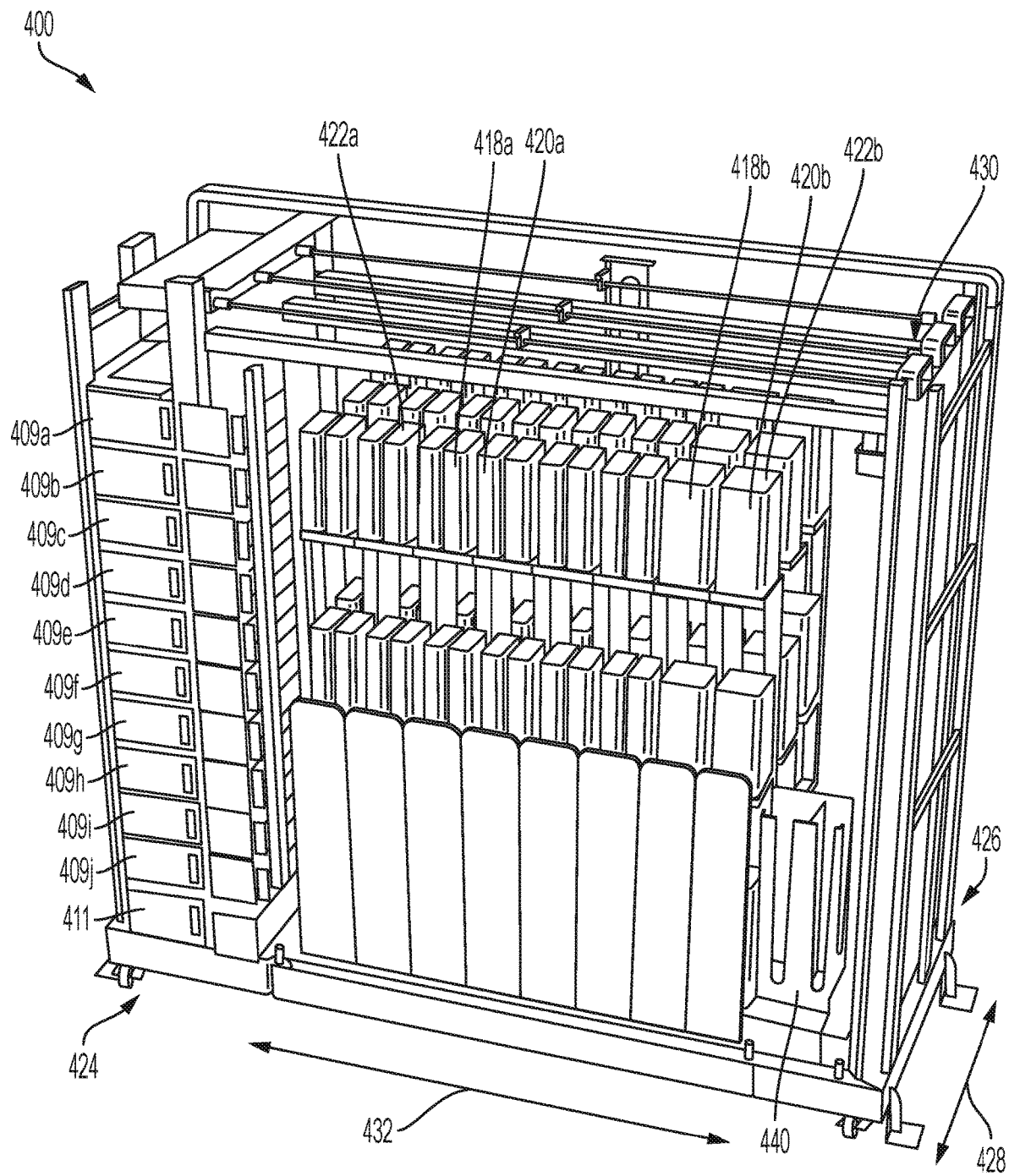
FIG. 14 is an illustration of an interior of the dispenser.

FIG. 14 is a perspective view of the interior space of the dispenser 400, with the enclosure surrounding the interior space not being present, including return door 406 being removed. In this view a holder 418a of a first size is shown with a first size slot 420a, and a holder 418b of a second, larger size, is shown with a second size slot 420b. In this embodiment two different sizes of holders 418 are shown, but in other embodiments, all holders 418 can be the same size, or the holders 418 can be three or more different sizes.

In each holder 418, a plurality of medical products 422 are stored in the plurality of holders 418, all within the interior space of the dispenser 400 In this view a medical product 422a of a first size substantially fits within holder 418a, while a medical product 422b of a second size substantially fits within holder 418b. As seen in FIG. 14, each holder 418 includes a plurality of medical products 422, which are stacked on top of each other vertically with the holder 418. The number of medical products 422 stored with each holder 418 can vary, from a single medical product to tens, or hundreds of medical products stacked vertically on top of each other. Also, each individual holder 418 may contain the same kind of medical product as one or more of the other individual holders 418 within the dispenser 400, or each individual holder 418 stores a unique medical product that no other holder stores.

In this embodiment, there are three rows of holders 418, arranged in rows from a front 424 of the dispenser 400 to a rear 426 of the dispenser 400, in the direction of arrow 428. However, in other embodiments, one, two, four or more rows of holders may be within the dispenser 400.

In this embodiment a restocking area 440 is also configured to move in the direction of arrow 428, so substantially align with any of the rows of holders 418. This restocking area 440 is further discussed below.

Corresponding to each row of holders 418 is a transport mechanism 430. In this embodiment, there are three transport mechanisms 430, however, in other embodiments, a single transport mechanism 430, two transport mechanisms 430, four transport mechanisms 430 or more may be included in the dispenser 400. The transport mechanism 430 is configured to move a medical product 422 from the holder 418 to the dispensing area 409 (shown as dispensing areas 409a-409j in FIG. 14) behind the corresponding openable doors 408. The transport mechanism 430 will be described and shown in more detail below, but each transport mechanism includes a first reader configured to scan an identifier on the medical product 422. Because the medical products 422 are stacked vertically on top of each other, the first reader of the transport mechanism 430 is configured to read the identifier on the medical product 422 vertically highest within the holder 418, and as discussed below, upon reading the identifier, move the vertically highest medical product 422 within the holder 418 to a dispensing area 409.

Each medical product 422 stored within the dispenser 400 include an identifier, such as a bar code, a QR code, and/or a Radio Frequency Identification (RFID). The dispenser includes one or more readers that are configured to read and record medical product 422, and store within the dispenser 400 relevant information regarding the medical product, such as a Stock Keeping Unit (SKU), the expiration of the medical product, the number of products within the package of medical product, etc. This information can be stored within the electronic storage device 413 of the dispenser and/or an external database through a communication with the dispenser 400. Along with the electronic storage device 413, the dispenser also includes a processor 415, a second communication interface 417 and the first communication interface 419. The second communication interface 417 and first communication interface 419 are configured to receive and transmit information to a database (and/or a cloud based service) in any suitable way, such as through one or more of a wired internet connection, a wireless internet connection, a cellular connection, a Bluetooth connection, a Near Field Communication connection, etc. Also, in some embodiments, the first communication interface 419 and the second communication interface 417 are a single device that is configured to receive and transmit, in other embodiments, "first" and "second" communication interfaces can be interchanged.

As used herein, the term "processor" may refer to, is part of, or includes circuitry capable of sequentially and automatically carrying out a sequence of arithmetic or logical operations; recording, storing, and/or transferring digital data. The term "processor" may refer to one or more application processors, one or more baseband processors, a physical central processing unit (CPU), a single o multiple-core processor, and/or any other device capable of executing or otherwise operating computer-executable instructions, such as program code, software modules, and/or functional processes.

As used herein, the term "electronic storage device" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

Each of the plurality of holders 418 are configured to support each of the plurality of medical products 422 in fixed locations, such that the electronic storage device 413 (and/or an external database through a communication with the dispenser 400) is also configured to store a location of each of the plurality of holders 418 within the dispenser 400 and associate each location of each of the plurality of holders 418 with one of the plurality of medical products 422.

During movement of the medical products 422, the first reader on the transport mechanism 430 is configured to read the identifier of the medical product 422 upon removal of the medical product 422 from the holder 418 and transmit to the electronic storage device 413 to subtract the removed medical product 422 from the available inventory of the medical product 422.

More medical products 422 are added the dispenser 400 in one of two ways.

A first way more medical products 422 are added to the dispenser 400 is through a replenishment method. Under this method a user carries one or more new medical products to the dispenser 400. The user then moves the new medical product, or a container storing one or more new medical products, to a position that a second reader can read the identifier of the new medical product or container storing one or more new medical products. This second reader can be on any portion of the dispenser 400 that is accessible by a user, which is also configured to scan the identifier of the new medical product. Alternatively, or in conjunction, the user can interact with the display 416 and manually enter the number and type of new medical product to be added to the dispenser 400.

The second reader can then transmit to the electronic storage device 413 of the dispenser 400 a quantity of the newly added medical product so that the electronic storage device 413 can update the available inventory value of that newly added medical product (by adding the amount of the newly added medical product to the previously stored medical product 422 of the same type).

Upon reading the identifier of the new medical product and transmitting the quantity of the newly added medical product to the electronic storage device 413, the user can move at least one of the left movable door 402 and the right movable door 404 from a closed position to an open position, so the user can access the interior space of the dispenser 400.

The user can then either review the display 416 (which can illustrate a planogram of the plurality of holders and indicate in some way which of the one or a ore holders 418 correspond to the newly added medical product) or visually check which of the one or more holders 418 is currently storing the same kind of medical product, and add the new medical product to the holder 418.

For new medical products that have not been previously stored within the dispenser 400, the display 416 may illustrate the planogram, and indicate an empty holder 418 and/or indicate a holder 418 having stored medical product that is to be removed first prior to addition of the new medical product.

A second way more medical products 422 are added to the dispenser 400 is through a restock method. Under this method, a user opens return door (406 of FIG. 12) to access restocking area 440. In other embodiments the restocking area 440 can be accesses in any other suitable way, such as through an opening in a side of the dispenser 400. The user then adds restocked medical product to the restocking area 440, such that the identifier of each restocked medical product is vertically upwards.

The restocked medical products can be medical products 422 that were previously dispensed for a procedure, but were not used, and are now returned and are to be added back to available inventory. The restocked medical products can also be new medical products that are to be added to the dispenser 400 for the first time.

As noted above, the restocking area 440 is configured to move between the front of the dispenser 424 and the back of the dispenser 426, and is configured to substantially align itself with a row of the plurality of holders 418. The restocking area 440 moves through a driving force delivered from any suitable source, such as an electric motor, etc.

Once a restocked medical product is within the restocking area 440, the first reader of the transport mechanism 430 is configured to read the identifier of the restocked medical product in the restocking area 440. This restocked medical product is not shown and therefore not numbered, and is referred to as "restocked medical" product when in the restocking area, and becomes medical product 422 upon restock, as discussed below.

The first reader of the transport mechanism 430 can be triggered to read the identifier of the restocked medical product under a number of circumstances. For example, the transport mechanism 430 can receive a notification from the display 416 or from the database (and/or a cloud based service) that there is medical product(s) to be restocked presently in the restocking area 440; the transport mechanism 430 can receive a periodic notification from the database (and/or a cloud based service) to move to the restocking area 440 at predetermined intervals to check if there is any restocked medical product(s) to be read; the transport mechanism 430 can, after fulfilling a pick list, then move to the restocking area 440 to check if there is any restocked medical product(s) to be read; the restocking area 440 may include a sensor (not shown) that detects when one or more medical products have been placed in the restocking area 440, and upon sensing, the processor 415 can notify the transport mechanism 430 there are restocked medical product(s) in the restocking area 440; and/or the return door 406 may include a sensor (not shown) that detects when the return door 406 is opened and closed, and upon sensing, the processor 415 can notify the transport mechanism 430 there are restocked medical product(s) in the restocking area 440.

Upon reading the identifier of the restocked medical product, the dispenser 400 (or the electronic storage device 413 of the dispenser 400, and/or an external database through a communication with the dispenser 400) identifies the type of restocked medical product and determines if it is the same kind of medical product as any of the currently stored medical products 422. If the restocked medical product is the same as one of the stored medical products 422 in the row of the transport mechanism 430, the transport mechanism 430 is configured to move the restocked medical product from the restocking area 440 to one selected holder of the plurality of holders 418 so that the restocked medical product rests vertically on top of the stack of medical products within the holder 418.

Figure 15:
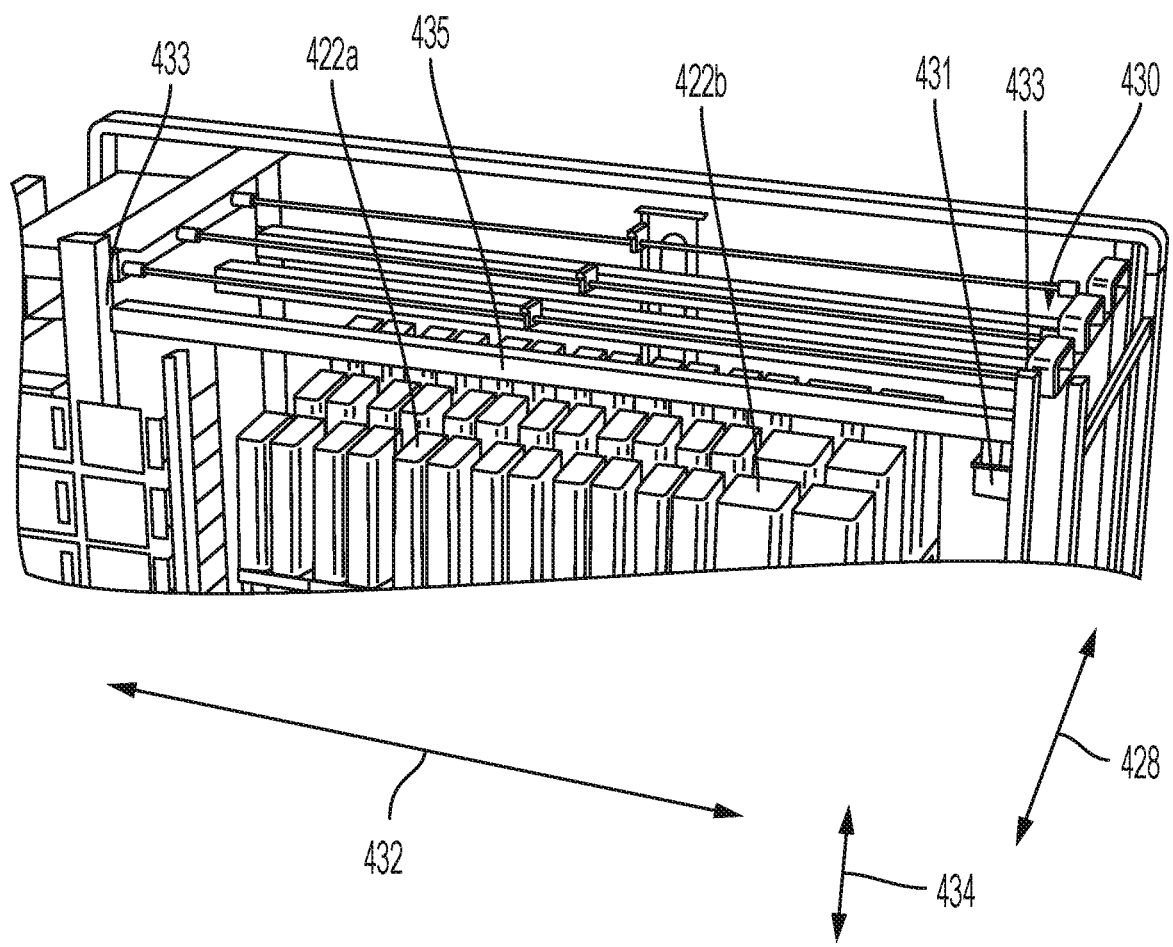
FIG. 15 is an illustration of a transport mechanism of the dispenser.

The transport mechanism 430 is shown in more detail in FIG. 15, which is a magnified view of a portion of the interior of dispenser 400. The transport mechanism 430 includes a pick head 431. This pick head 431 includes the first reader, which is configured to scan an identifier on the restocked medical product, on a lower surface of the pick head 431 (shown in a later figure), which faces the restocked medical product in the restocking area 440.

The pick head 431 is moved vertically, closer to or further from the restocking area, in the direction of arrow 434. This movement is effected through a driving force delivered from any suitable source, such as an electric motor, etc, that causes the pick head 431 to more vertically along vertical transport rails 433. Once pick head 431 is sufficiently close to the restocking area 440 and restocked medical product the first reader reads the identifier of the vertically highest restocked medical product in the restocking area 440. After reading, the pick head 431 moves further vertically downwards towards the restocked medical product, applies a negative pressure (or suction force) through a suction head (shown in FIGS. 16A-16C) that extends from the lower surface of the pick head 431, until the suction head contacts or nearly contacts the restocked medical product, causing the restocked medical product to be secured to the suction head of the pick head 431. The suction head can be any suitable shape and structure, and can be formed of any suitable pliable, compliant, rigid or semi-rigid material and which can include an opening for delivery of a suction pressure to a portion of a medical product. A vacuum or any other suitable mechanism can provide the negative pressure to the pick head 431.

Upon securing the restocked medical product to the suction head of the pick head 431, the pick head 431 moves vertically upwards on vertical transport rails 433, so that it is vertically higher than the upper surface of the holders 418. The pick head 431 (and secured, restocked medical product) moves horizontally in the direction of arrow 432, along horizontal transport rail 435 until the restocked medical product is vertically above the selected holder 418.

Once vertically above the selected holder 418, the pick head 431 (and secured, restocked medical product) moves vertically down along vertical transport rails 433 until the restocked medical product contacts or nearly contacts the upper surface of the vertically highest medical product 422 in the selected holder 418. The negative pressure is then ceased, and the restocked medical product becomes unsecured from the pick head 431, and rests on the upper surface of the vertically highest medical product 422 within the holder 418, the restocked medical product itself becoming the vertically highest medical product 422 within the selected holder 418.

The method steps discussed above are repeated for each restocked medical product in the restocking area 440.

If the restocked medical product is the same kind of medical product as one of the currently stored medical products 422, but that same kind of medical product is in a different row, the restocking area 440 will move and align itself with the correct row, so that the correct row's transport mechanism 430 can move the restocked medical product to the selected holder of the holders 418.

At any point between reading the identifier of the restocked medical product and movement of the restocked medical product to the selected holder, the dispenser 400 (or the electronic storage device 413 of the dispenser 400, and/or an external database through a communication with the dispenser 400) receives the read identifier and adds the restocked medical product to the available inventory of the medical product 422 within the dispenser 400.

The selected holder of holders 418 the restocked medical product is to be added to is determined by the dispenser (or the electronic storage device 413 of the dispenser 400, and/or an external database through a communication with the dispenser 400) by matching the identified restocked medical product to one of the plurality of stored medical products stored in the electronic storage device 413 (and/or an external database through a communication with the dispenser 400), and then assigning the selected holder (of holders 418) to the associated location of the matched one of the plurality of stored medical products of the electronic storage device 413.

After the restocked medical product is moved from the restocking area 440 to a holder 418, the first reader can again read the identifier of a subsequent restocked medical product in the restocking area 440 and go through the above movement of the restocked medical product, until no restocked medical products are within restocking area 440.

Medical products can also be moved to the single error area 411 of FIG. 14 upon return to the restocking area 440 if the medical product(s) were not included in a previous pick list. In this example, upon scanning the restocked medical product, the processor 415 of the dispenser 400 can review internally stored pick lists, or the first communication interface 419 of the dispenser 400 can transmit the type of restocked medical product to an external database that maintains a record of pick lists. The restocked medical product can then be compared to one or more previous pick lists to determine if the dispenser 400 had previously dispensed that restocked medical product. If the dispenser 400 did not previously dispense that restocked medical product (based on the comparison between the restocked medical product and the one or more previous pick lists indicating no matching medical product on the one or more previous pick lists), that restocked medical product can be moved to the single error area 411. If the dispenser 400 did previous dispense that restocked medical product (based on the comparison between the restocked medical product and the one or more previous pick lists indicating a matching medical product on the one or more previous pick lists) the restocked medical product is moved to the selected holder of holders 418.

As another example, medical products can also be moved to the single error area 411 upon return to the restocking area 440 if the medical product(s) are not indicated as being scheduled for restocking. In this example, after a pick list is completed, and the medical product(s) are removed from the dispenser 400, the medical product(s) are then brought to the location of surgical procedure. Upon completion of the surgical procedure, a user on a computing device, can indicate if one or more of the dispensed medical products were not used. The computing device can then transmit that information to the dispenser 400 (and/or an external database through a communication with the dispenser 400) as a restock notice.

Upon scanning the restocked medical product, the processor 415 of the dispenser 400 can review internally stored restock notices, or the first communication interface 419 of the dispenser 400 can transmit the type of restocked medical product to an external database that maintains a record of restock notices. The restocked medical product can then be compared to one or more previous restock notices to determine if the restocked medical product is present on any restock notice. If the restocked medical product is not present on a restock notice, that restocked medical product can be moved to the single error area 411. If the restocked medical product is present on a restock notice the restocked medical product is moved to the selected holder of holders 418.

If the restocked medical product is determined as not being the same kind of medical product as one of the currently stored medical products 422, the transport mechanism 430 is configured to move the restocked medical product that is not the same to the single error area 411. All movement of restocked medical products is effected with the transport mechanism 430, as discussed below.

The second communication interface 417 of the dispenser 400 is configured to receive various signals and data, including an available inventory request, a pick list and a recall request.

If the second communication interface 417 of the dispenser 400 receives an available inventory request, the processor 415 can access the electronic storage device 413 (and/or an external database through a communication with the dispenser 400) and determine the available inventory, which is an updated total of all restocked medical products in addition to all replenished medical products, minus all dispensed medical products and minus all medical products moved to the single error area 411. Once the available inventory is determined, the first communication interface 419 of the dispenser 400 is configured to transmit the available inventory, in response to the available inventory request, to a database. This database can be at another location within the same building the dispenser 400 is in, or in a separate location. Further, the second communication interface 417 and first communication interface 419 are configured to receive and transmit information to the database in any suitable way, such as through one or more of a wired internet connection, a wireless internet connection, a cellular connection, a Bluetooth connection, a Near Field Communication connection, etc.

The second communication interface 417 of the dispenser 400 can also receive a pick list. The pick list is a list of one or more medical products of the plurality of medical products 422 that are to be moved from the holders 418 to a respective dispensing area 409. Thus, upon receipt of the pick list, the dispenser 400 determines the location of each holder 418 that the one or more medical products on the fulfillment list is associated with, and the number of medical products on the fulfillment list at each holder 418 location.

The transport mechanism 430 then moves to the location of each of the associated holders 418 and successively secures each of the vertically highest medical product 422, moving each of the secured medical products 422 to a dispensing area 409.

The transport mechanism 430 secures each medical product 422 by moving vertically downwards on vertical transport rails 433 from the position shown in FIG. 14, once the pick head 431 is in the correct horizontal position above the located holder 418. The pick head 431 moves vertically downwards until the suction head of the pick head 431 contacts or nearly contacts the upper surface of the vertically highest medical product 422 in the selected holder 418. A negative pressure is then applied through the suction head of the pick head 431, causing the vertically highest medical product 422 to be secured to the suction head of the pick head 431.

The pick head 431 (and the secured medical product 422) is moved vertically upwards and horizontally towards the dispensing areas 409a-409j. Each of the dispensing areas 409a-409j includes an opening, and a ramp that extends towards the pick head 431, so that upon vertical alignment with the correct dispensing area 409, the secured medical product can be unsecured, contact the ramp, and slide into the correct dispensing area 409. To unsecure the medical product a negative pressure is ceased, and the medical product 422 becomes unsecured from the suction head of the pick head 431. The correct ramp is selected through a communication received by the dispenser 400, through second communication interface 417, that one of the plurality of dispensing areas 409a-409j are empty and able to receive a new medical product(s) of a pick list.

The above description can pertain to when the dispenser 400 includes one transport mechanism 430 (and thus one pick head 431), however, a plurality of transport mechanisms 430 may be included in dispenser 400 (for example three are shown in the present figures). When there are a plurality of transport mechanisms 430, upon receipt of the pick list, the dispenser 400 determines the location of each holder 418 that the one or more medical products on the fulfillment list is associated with, determines which transport mechanism 430 of the plurality of transport mechanisms each holder 418 is aligned with, and the number of medical products on the fulfillment list at each holder 418 location. Then, one or more of the transport mechanisms 430 that are in alignment with teach holder 418 location move to the location of each of the associated holders 418 and successively secures each of the vertically highest medical product 422, moving each of the secured medical products 422 to a dispensing area 409.

The dispensing area 409 the medical products of the pick list are moved to is a dispensing area 409 that does not include other medical products. For example, the dispensing area 409 the medical products of the pick list are moved to is a dispensing area 409 that has previously been emptied by a user after a previous pick list has been fulfilled.

The second communication interface 417 of the dispenser 400 can also receive a recall request. The recall request is a list of one or more medical products of the plurality of medical products 422 (or restocked medical products) have been recalled. To avoid the possibility that the medical products 422 will be dispensed as part of a pick list, the dispenser 400 determines the location of each holder 418 that the one or more medical products on the recall list is associated with, and the number of medical products on the fulfillment list at each holder 418 location.

The transport mechanism 430 then moves to the location of each of the associated holders 418 and successively secures each of the vertically highest medical product 422, moving each of the secured medical products 422 to the single error area 411.

The transport mechanism 430 secures each medical product 422 by moving vertically downwards on vertical transport rails 433 from the position shown in FIG. 14, once the pick head 431 is in the correct horizontal position above the located holder 418. The pick head 431 moves vertically downwards until the suction head of the pick head 431 contacts or nearly contacts the upper surface of the vertically highest medical product 422 in the selected holder 418. A negative pressure is then applied through the suction head of the pick head 431, causing the vertically highest medical product 422 to be secured to the suction head of the pick head 431.

The pick head 431 (and the secured medical product 422) is moved vertically upwards and horizontally towards the error area 411. The error area 411 includes an opening, and a ramp that extends towards the pick head 431, so that upon vertical alignment with the error area 411, the secured medical product can be unsecured, contact the ramp, and slide into the error area 411. To unsecure the medical product a negative pressure is ceased, and the medical product 422 becomes unsecured from the suction head of the pick head 431.

The pick head 431 can continue to successively move all medical products 422 from their respective holders 418, each time securing the vertically highest medical product 422 within the holder 418, until all medical products 422 that are on the recall list have been moved to the error area 411. If a medical product 422, which is on the recall list, is not accessible by the pick head 431, for example if a medical product 422 that is not on the recall list is vertically above the medical product 422 that is on the recall list, the dispenser 400 can provide an error message on the display 416 and/or send an error signal to a database. The dispenser 400 can also, if the medical product 422 that is not on the recall list is present vertically above the medical product 422 that is on the recall list, upon the medical product 422 that is not on the recall list being moved, the dispenser 400 can then cause the pick head 431 to move the medical product 422 that is on the recall list to the single error area 411.

Figure 16A:
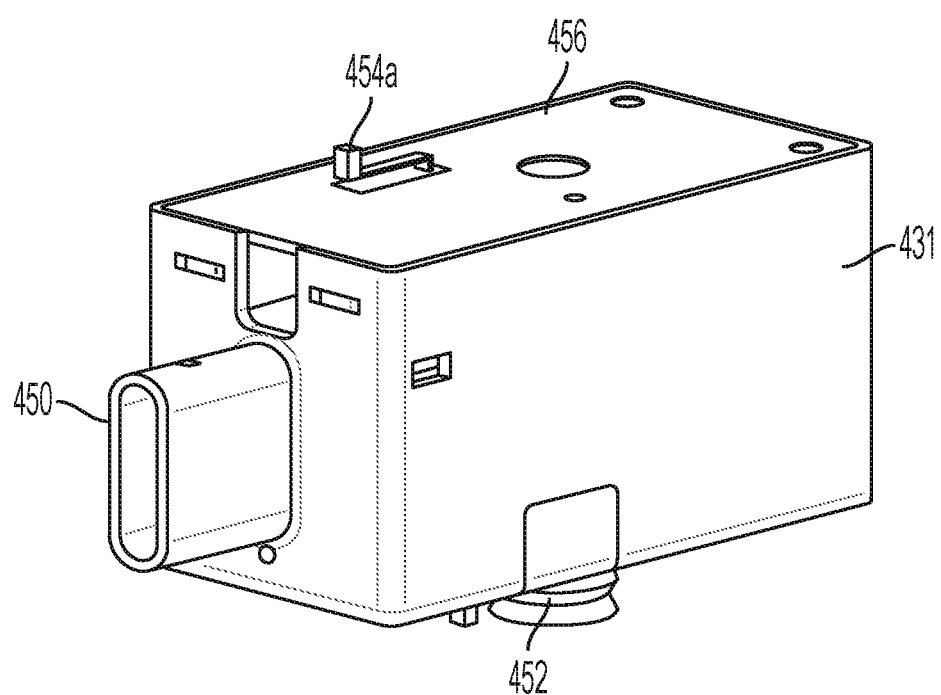
FIGS. 16A-16C are illustrations of a pick head.
Figure 16B:
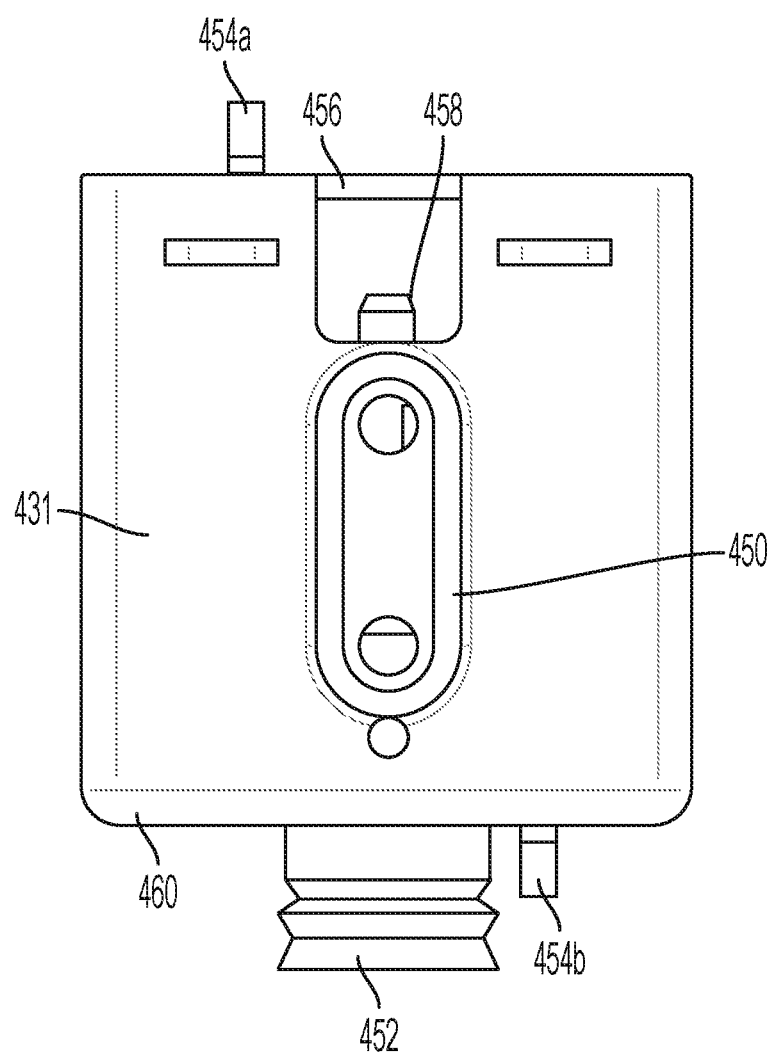
Figure 16C:
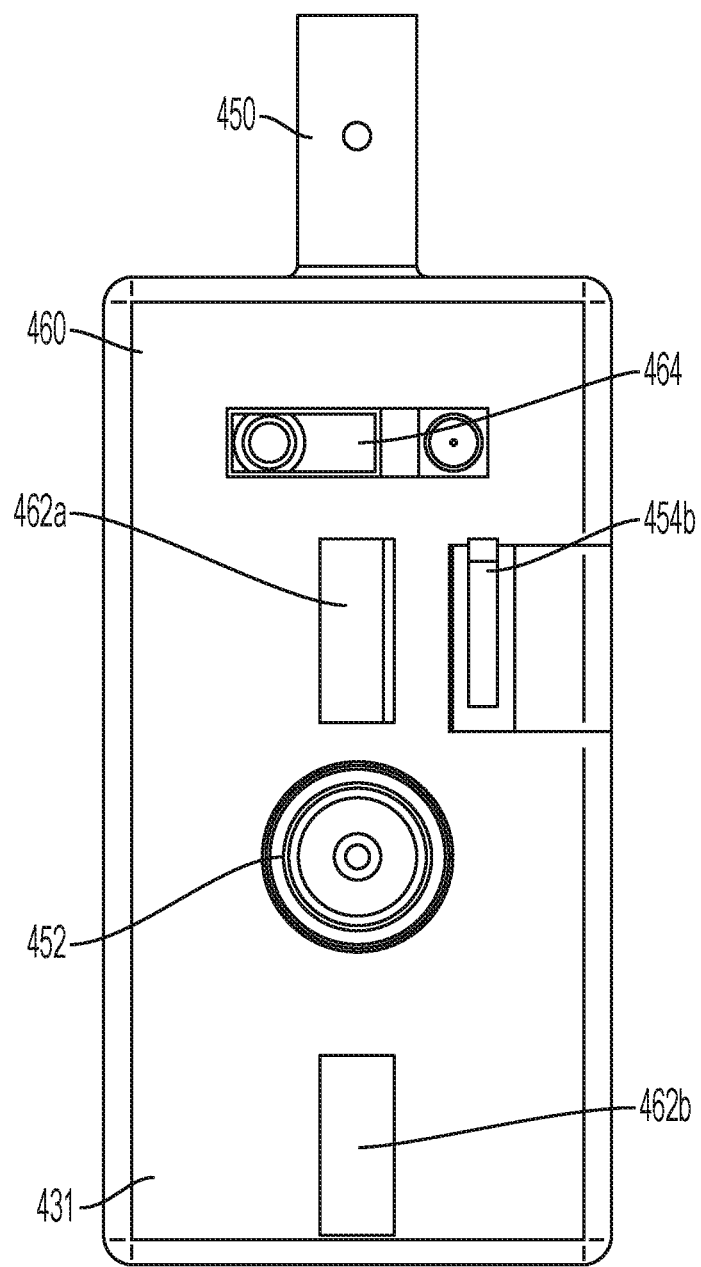

A detailed view of the pick head 431 is shown in FIGS. 16A-16C. In FIG. 16A, a perspective view of the pick head 431 is shown, removed from the dispenser 400.

The pick head 431 includes a suitable connector 450, which is capable of connecting the pick head 431 to the horizontal transport rail 435. Suction head 452 extends from a lower surface of the pick head 431, and is better shown in later figures. The pick head 431 also includes a physical stop element 454a that extends from an upper surface 456. The physical stop element 454a is a physical element that, upon contact with another object, is configured to signal the pick head 431 to not move further in the vertical direction by causing a driving motor of the pick head 431 to stop.

FIG. 16B is a side view of pick head 431. From this view a gas fitting 458 can be seen. The suction head 452 receives a negative pressure through a suction force received through the gas fitting 458 (connecting hoses not shown).

A physical stop element 454b also extends from a lower surface 460 of the pick head 431. During operation of the pick head 431, the physical stop element 454b is a predetermined distance from the medical product in the holder upon the medical product being secured to the suction head 452. The physical stop element 454b is a physical element that, upon contact with another object (such as a medical product), is configured to signal the pick head 431 to not move further in the vertical direction by causing a driving motor of the pick head 431 to stop.

FIG. 16C is a view of the lower surface 460 of the pick head 431. In addition to the suction head 4522 and physical stop element 454b, the lower surface 460 can include a first reader 462a and/or a first reader 462b. In other embodiments only one first reader, or three or more first readers can be included on the lower surface 460. The first reader 462a/462b can be any reader capable of reading the identifier of a medical product such as a bar code reader, a QR code reader, a Radio Frequency Identification (RFID) reader, etc.

Also seen in a sensor 464. This sensor 464 can be any sensor, including but not limited to an infrared sensor (passive or otherwise), a light level sensor, a photodiode, a motion detector, a temperature sensor, a humidity sensor, an optical sensor, and a CCD/CMOS camera.

The sensor 464 can be used in conjunction with physical stop element 454b, or instead of physical stop element 454b as the stop mechanism. The sensor 464 can be configured to determine the location (through communication with the processor 415, or an additional processor) of the pick head 431 in relation to an object (such as a medical product), so that once the pick head 431 reaches a predetermine position in relation to the object, the sensor 464 is configured to signal the pick head 431 to not move further in the vertical direction by causing a driving motor of the pick head 431 to stop.

The stop mechanism of either or both of physical stop element 454b and sensor 464 are included so that the picking head moves to a vertical location suitable for successively picking up medical products from the holders.

The recall list can also be referred to by the dispenser upon receipt of a restocked medical product. If the restocked medical product is part of the recall list, the transport mechanism 430 can move the restocked medical product directly from the restocking area 440 to the error area 411.

The second communication interface 417 can also receive a status request from a cloud based service, at various times, or at specific intervals. Upon receipt of this status request, the first communication interface 419 can transmit back to the cloud based service that the dispenser 400 is operating with a suitable power source (through a connection with a wall socket and/or a battery) and that the dispenser is connected to the internet (through a wired and/or wireless connection).

Each of the above dispensers is configured with sufficient hardware processors to communicate with an internal storage, a local database and/or a cloud based service. The cloud based service is any service configured to interact, receive, store, and transmit data among many devices in differing locations.

At any time inventory in any of the dispensers discussed above can be transmitted to the database, so that other entities that have access to database can track usage of medical products by the identification of the accessing user, and can track inventory of the dispenser. The database can also transmit, at any time, inventory information to the dispenser that, for example, a medical product has been recalled or is expired. The dispenser could then display such data on the user interface, or an accessing user can be notified of such information.

Although not discussed above, each of the above dispenser can include a sterilizer to provide sterilization to the interior of each dispenser, and/or to provide sterilization to each medical product being stocked into the dispenser. Different levels of sterilization may be selected through an interaction with the graphical user interface, with a higher level being selectable for medical products that were unused in a surgical room and are now being restocked into the dispenser.

Although not discussed above, each of the above dispensers can include a temperature monitor and/or a humidity monitor. The dispenser can be configured to record temperatures and humidities within the dispenser at various times, and transmit such recordings to a database.

The phrase "communication interface" includes electronic circuitry, configured for one or more specific standards, that enables one device to telecommunicate (transmit and/or receive) with another device.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A dispenser, the dispenser comprising:
a movable door, movable between an open position, and a closed position, when the movable door is in the open position, the dispenser is configured to receive a medical product into an interior space of the dispenser, wherein the medical product comprises an identifier;
a holder in the interior space, the holder configured to store the medical product in a fixed location;
a dispensing area configured to hold a medical product, wherein the dispenser further comprises an openable door extending over the dispensing area;
a transport mechanism configured to move the medical product from the holder to the dispensing area, wherein the transport mechanism comprises a first reader configured to scan the identifier;
a processor;
an error area, wherein the error area is configured to hold at least one medical product;
an error door extending over the error area; and
an electronic storage device, wherein
the electronic storage device is configured to store a location of the holder within the dispenser,
at least one of the first reader and a second reader, the second reader configured to read the identifier, being configured to read the identifier of the medical product upon insertion of the medical product into the dispenser, or configured to read the identifier of a container storing one or more medical products, and store a quantity of the medical product in the electronic storage device as an available inventory of medical product, and wherein
the first reader is configured to read the identifier of the medical product upon removal of the medical product from the holder and transmit to the electronic storage device to subtract the removed medical product from the available inventory of the medical product.

2. The dispenser of claim 1, wherein the dispenser comprises a plurality of medical products stored in a plurality of holders in the interior space, wherein each of the plurality of holders is configured to support each of the plurality of medical products in fixed locations, respectively, and wherein the electronic storage device is configured to store a location of each of the plurality of holders within the dispenser and associate each location of each of the plurality of holders with one of the plurality of medical products.

3. The dispenser of claim 1, further comprising a restocking area.

4. The dispenser of claim 3, wherein the restocking area is configured to move between a front of the dispenser and a back of the dispenser from a front of the dispenser to a back of the dispenser, and is configured to substantially align itself with a row of the plurality of holders.

5. The dispenser of claim 3, wherein the first reader is configured to read the identifier of a restocked medical product in the restocking area.

6. The dispenser of claim 5, wherein the dispenser is configured to identify the restocked medical product, and if the restocked medical product is the same as one of the plurality of stored medical products, the transport mechanism is configured to move the restocked medical product to the location of the one selected holder of the plurality of holders, and the dispenser is configured to add the restocked medical product to the available inventory of the medical product.

7. The dispenser of claim 6, wherein the location of the one selected holder is selected by matching the identified restocked medical product to one of the plurality of stored medical products stored in the electronic storage device, assigning the selected holder to the associated location of the matched one of the plurality of stored medical products.

8. The dispenser of claim 5, wherein the dispenser is configured to identify the restocked medical product, and if the restocked inventory is not the same as one of the plurality of stored medical products, the transport mechanism is configured move the restocked medical product to the error area.

9. The dispenser of claim 5, further comprising a second communication interface, wherein the second communication interface is further configured to transmit, to a database, that an error is determined based on the identifier, wherein the error is selected from the group consisting of an identifier is unreadable, an identifier that indicates that the restocked medical product is recalled, an identifier that indicates that the restocked medical product does not correspond to any other medical product in the dispenser, and an identifier that indicates that the restocked medical product is expired.

10. The dispenser of claim 9, wherein if the error is determined, the transport mechanism moves the restocked medical product to the error area.

11. The dispenser of claim 1, further comprising a display configured to receive an input contact from a user, wherein the contact is used to receive a code, receive a selection for a video recording, display received video, receive signals from the electronic storage device, display data selected from the group consisting of a number of each of the plurality of medical products within the dispenser, a location of each of the plurality of holders, and which medical product of the plurality of medical products is stored in each of the plurality of holders.

12. The dispenser of claim 1, further comprising a plurality of dispensing areas.

13. The dispenser of claim 12, wherein for each of the plurality of dispensing areas the dispenser comprises a respective screen, wherein each of the respective screens is configured to receive signals from the electronic storage device and is configured to display dispensing area identifying information.

14. The dispenser of claim 12, wherein for each of the plurality of dispensing areas, the dispenser comprises a respective button configured to receive a response, wherein the response is selected from the group consisting of an input force from a user, an input contact from the user, and/or an input of near physical contact within a predetermined proximity, wherein the dispenser is configured to transmit to a database that the response was received by the button.

15. The dispenser of claim 14, wherein each of the buttons comprises a light source configured to illuminate in at least three different colors upon receipt of a signal, wherein one of the at least three different colors indicates that a pick list is complete, one of the at least three different colors indicates that a pick list is incomplete, and one of the at least three different colors indicating a pick list is complete but that at least one of the medical products in the dispensing area is different from the medical product of the pick list.

16. The dispenser of claim 1, further comprising a first communication interface, the first communication interface configured to receive at least one of an available inventory request, a pick list and a recall request.

17. The dispenser of claim 16, further comprising a second communication interface, wherein the second communication interface is configured to transmit the available inventory, in response to the available inventory request, to a database.

18. The dispenser of claim 16, wherein the pick list is a list of one or more medical products of the plurality of medical products, wherein upon receipt of the pick list the dispenser determines the location of each holder of the one or more medical products of the list is associated with and the number of medical products on the list at each location, and then causes the transport mechanism to move to the location of each holder, successively secure each medical product of the pick list, and move each of the secured medical products to the dispensing area.

19. The dispenser of claim 18, wherein the transport mechanism secures each medical product by contacting each medical product, and applies a negative pressure sufficient to maintain contact to each medical product.

20. The dispenser of claim 16, wherein the recall request is a list of one or more medical products of the plurality of medical products, wherein upon receipt of the recall request the dispenser determines the location of each holder the one or more medical products of the list is associated with and the number of medical products on the list at each location, and then causes the transport mechanism to move to the location of each holder, successively secure each medical product of the recall list that is accessible, and move the secured medical product to the error area.

21. The dispenser of claim 20, wherein the transport mechanism secures each medical product by contacting each medical product, and applies a negative pressure sufficient to maintain contact to each medical product.

22. The dispenser of claim 16, further comprising a plurality of transport mechanisms.

23. The dispenser of claim 22, wherein the pick list is a list of one or more medical products of the plurality of medical products, wherein upon receipt of the pick list the dispenser determines the location of each holder of the one or more medical products of the list is associated with, which transport mechanism of the plurality of transport mechanisms is aligned with each holder and the number of medical products on the list at each location, and then causes one or more of the plurality of transport mechanisms to move to the location of each holder, successively secure each medical product of the pick list, and move each of the secured medical products to the dispensing area.

24. The dispenser of claim 1, wherein the transport mechanism comprises a stop mechanism, wherein the stop mechanism is at least one of a physical element that contacts an object and causes a driving motor of the transport mechanism to stop and a sensor that determines the location of the transport mechanism and causes the driving motor of the transport mechanism to stop once the transport mechanism reaches a predetermined position, wherein the physical element and the predetermined position are a predetermined distance from the medical product in the holder.

25. A dispenser, the dispenser comprising:
a movable door, movable between an open position, and a closed position, when the movable door is in the open position, the dispenser is configured to receive a medical product into an interior space of the dispenser, wherein the medical product comprises an identifier;
a holder in the interior space, the holder configured to store the medical product in a fixed location;
a dispensing area configured to hold a medical product, wherein the dispenser further comprises an openable door extending over the dispensing area;
a transport mechanism configured to move the medical product from the holder to the dispensing area, wherein the transport mechanism comprises a first reader configured to scan the identifier;
a processor;
a plurality of dispensing areas, wherein for each of the plurality of dispensing areas, the dispenser comprises a respective button configured to receive a response, wherein the response is selected from the group consisting of an input force from a user, an input contact from the user, and/or an input of near physical contact within a predetermined proximity, wherein the dispenser is configured to transmit to a database that the response was received by the button; and
an electronic storage device, wherein
the electronic storage device is configured to store a location of the holder within the dispenser,
at least one of the first reader and a second reader, the second reader configured to read the identifier, being configured to read the identifier of the medical product upon insertion of the medical product into the dispenser, or configured to read the identifier of a container storing one or more medical products, and store a quantity of the medical product in the electronic storage device as an available inventory of medical product, and wherein
the first reader is configured to read the identifier of the medical product upon removal of the medical product from the holder and transmit to the electronic storage device to subtract the removed medical product from the available inventory of the medical product.

26. A dispenser, the dispenser comprising:
a restocking area;
a movable door, movable between an open position, and a closed position, when the movable door is in the open position, the dispenser is configured to receive a medical product into an interior space of the dispenser, wherein the medical product comprises an identifier;
a holder in the interior space, the holder configured to store the medical product in a fixed location;
a dispensing area configured to hold a medical product, wherein the dispenser further comprises an openable door extending over the dispensing area;
a transport mechanism configured to move the medical product from the holder to the dispensing area, wherein the transport mechanism comprises a first reader configured to scan the identifier, wherein the first reader is configured to read the identifier of a restocked medical product in the restocking area;
a processor;
a communication interface, wherein the communication interface is configured to transmit, to a database, that an error is determined based on the identifier, wherein the error is selected from the group consisting of an identifier is unreadable, an identifier that indicates that the restocked medical product is recalled, an identifier that indicates that the restocked medical product does not correspond to any other medical product in the dispenser, and an identifier that indicates that the restocked medical product is expired; and an electronic storage device, wherein
the electronic storage device is configured to store a location of the holder within the dispenser,
at least one of the first reader and a second reader, the second reader configured to read the identifier, being configured to read the identifier of the medical product upon insertion of the medical product into the dispenser, or configured to read the identifier of a container storing one or more medical products, and store a quantity of the medical product in the electronic storage device as an available inventory of medical product, and wherein
the first reader is configured to read the identifier of the medical product upon removal of the medical product from the holder and transmit to the electronic storage device to subtract the removed medical product from the available inventory of the medical product.

* * * * *